United States Patent
Zhao et al.

(10) Patent No.: US 11,778,340 B2
(45) Date of Patent: *Oct. 3, 2023

(54) MULTI-FUNCTION IMAGING

(71) Applicant: Intuitive Surgical Operations, Inc., Sunnyvale, CA (US)

(72) Inventors: Wenyi Zhao, Weston, FL (US); Jeffrey M. DiCarlo, Austin, TX (US); Ian E. McDowall, Woodside, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/829,000

(22) Filed: May 31, 2022

(65) Prior Publication Data

US 2022/0294995 A1    Sep. 15, 2022

Related U.S. Application Data

(63) Continuation of application No. 17/160,077, filed on Jan. 27, 2021, now Pat. No. 11,381,759, which is a
(Continued)

(51) Int. Cl.
*H04N 13/257* (2018.01)
*H04N 25/13* (2023.01)
(Continued)

(52) U.S. Cl.
CPC ......... *H04N 25/134* (2023.01); *A61B 1/0005* (2013.01); *A61B 1/00006* (2013.01); *A61B 1/00009* (2013.01); *A61B 1/00193* (2013.01); *A61B 1/043* (2013.01); *A61B 1/05* (2013.01); *A61B 1/06* (2013.01); *A61B 1/0638* (2013.01); *A61B 1/0646* (2013.01); *G06T 3/4015* (2013.01); *H04N 5/265* (2013.01); *H04N 13/257* (2018.05); *H04N 23/10* (2023.01); *H04N 23/45* (2023.01); *H04N 23/56* (2023.01); *H04N 23/57* (2023.01); *H04N 23/555* (2023.01)

(58) Field of Classification Search
USPC .......................................................... 348/68
See application file for complete search history.

(56) References Cited

U.S. PATENT DOCUMENTS 4,074,306 A   2/1978  Kakinuma et al.
4,873,572 A  10/1989  Miyazaki et al.
(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Behrooz M Senfi

(57) ABSTRACT

An example method includes receiving a single frame comprising a first set of pixel data that includes a fluorescence scene component and a second set of pixel data that includes a combination of a visible color component scene and the fluorescence scene component; and generating, based on the first set of pixel data that includes the fluorescence scene component and the second set of pixel data that includes the combination of the visible color component scene and the fluorescence scene component, a display scene.

20 Claims, 10 Drawing Sheets

Related U.S. Application Data continuation of application No. 16/697,507, filed on Nov. 27, 2019, now Pat. No. 10,944,919, which is a continuation of application No. 16/264,650, filed on Jan. 31, 2019, now Pat. No. 10,531,017, which is a continuation of application No. 15/965,017, filed on Apr. 27, 2018, now Pat. No. 10,237,497, which is a continuation of application No. 15/008,215, filed on Jan. 27, 2016, now Pat. No. 9,992,428, which is a continuation of application No. 13/893,536, filed on May 14, 2013, now Pat. No. 9,277,205.

(60) Provisional application No. 61/646,727, filed on May 14, 2012, provisional application No. 61/646,710, filed on May 14, 2012.

(51) Int. Cl.
| | | |
|---|---|---|
| *A61B 1/00* | (2006.01) | |
| *A61B 1/04* | (2006.01) | |
| *A61B 1/05* | (2006.01) | |
| *A61B 1/06* | (2006.01) | |
| *H04N 23/10* | (2023.01) | |
| *H04N 23/45* | (2023.01) | |
| *H04N 23/56* | (2023.01) | |
| *H04N 23/57* | (2023.01) | |
| *G06T 3/40* | (2006.01) | |
| *H04N 5/265* | (2006.01) | |
| *H04N 23/50* | (2023.01) | |

(56) References Cited

U.S. PATENT DOCUMENTS

| | | |
|---|---|---|
| 5,231,464 A | 7/1993 | Ichimura et al. |
| 6,331,181 B1 | 12/2001 | Tierney et al. |
| 6,760,058 B2 | 7/2004 | Hakamata |
| 6,837,883 B2 | 1/2005 | Moll et al. |
| 8,007,433 B2 | 8/2011 | Iketani |
| 8,167,793 B2 | 5/2012 | Scott et al. |
| 8,169,468 B2 | 5/2012 | Scott et al. |
| 8,228,368 B2 | 7/2012 | Zhao et al. |
| 8,605,148 B2 | 12/2013 | Robertson |
| 8,764,633 B2 | 7/2014 | McDowall |
| 8,810,631 B2 | 8/2014 | Scott et al. |
| 9,258,549 B2 | 2/2016 | DiCarlo et al. |
| 9,277,205 B2 * | 3/2016 | Zhao .................. H04N 9/04557 |
| 9,403,855 B2 | 8/2016 | Wong et al. |
| 9,992,428 B2 * | 6/2018 | Zhao .................... H04N 5/2258 |
| 10,237,497 B2 * | 3/2019 | Zhao ...................... H04N 5/265 |
| 10,531,017 B2 * | 1/2020 | Zhao .................... H04N 5/2256 |
| 10,944,919 B2 * | 3/2021 | Zhao ...................... H04N 5/265 |
| 11,381,759 B2 * | 7/2022 | Zhao ...................... H04N 9/045 |
| 2005/0203338 A1 | 9/2005 | Couvillon, Jr. et al. |
| 2006/0164500 A1 | 7/2006 | Marumoto |
| 2007/0156037 A1 | 7/2007 | Pilon et al. |
| 2008/0065105 A1 | 3/2008 | Larkin et al. |
| 2008/0091064 A1 | 4/2008 | Laser |
| 2009/0118578 A1 | 5/2009 | Takasugi et al. |
| 2010/0079587 A1 | 4/2010 | Yoshida |
| 2010/0322492 A1 | 12/2010 | Stepp et al. |
| 2012/0253157 A1 | 10/2012 | Yamaguchi et al. |
| 2013/0038689 A1 | 2/2013 | McDowall |
| 2013/0041221 A1 | 2/2013 | McDowall et al. |
| 2013/0041226 A1 | 2/2013 | McDowall |
| 2015/0073433 A1 | 3/2015 | Schaerer et al. |
| 2021/0152752 A1 | 5/2021 | Zhao et al. |

\* cited by examiner ial Applications

This application is a continuation of U.S. patent application Ser. No. 17/160,077 (filed 27 Jan. 2021), which is a continuation of U.S. patent application Ser. No. 16/697,507 (filed 27 Nov. 2019; now U.S. Pat. No. 10,944,919), which is a continuation of U.S. patent application Ser. No. 16/264,650 (filed 31 Jan. 2019; now U.S. Pat. No. 10,531,017), which is a continuation of U.S. patent application Ser. No. 15/965,017 (filed 27 Apr. 2018; now U.S. Pat. No. 10,237,497), which is a continuation of U.S. patent application Ser. No. 15/008,215 (filed 27 Jan. 2016; now U.S. Pat. No. 9,992,428), which is a continuation of U.S. patent application Ser. No. 13/893,536 (filed 14 May 2013; now U.S. Pat. No. 9,277,205), which claims priority to and the benefit of:

U.S. Provisional Application No. 61/646,710, filed May 14, 2012; and
U.S. Provisional Application No. 61/646,727, filed May 14, 2012, all of which are incorporated herein by reference in their entirety.
U.S. patent application Ser. No. 17/160,077 is related to U.S. patent application Ser. No. 13/893,550, which is incorporated by reference in its entirety.

BACKGROUND

Field of Invention

Aspects of this invention are related to endoscopic imaging, and are more particularly related to blending visible and alternate images so as to provide an enhanced real-time video display for a surgeon.

Related Art

The da Vinci® Surgical Systems, commercialized by Intuitive Surgical, Inc., Sunnyvale, Calif., are minimally invasive teleoperated surgical systems that offer patients many benefits, such as reduced trauma to the body, faster recovery and shorter hospital stay. One key component of a da Vinci® Surgical System (e.g., the model IS3000, da Vinci® Si HD) is a capability to provide two-channel (i.e., left and right) video capture and display of visible images to provide stereoscopic viewing for the surgeon. Such electronic stereoscopic imaging systems may output high definition video images to the surgeon, and may allow features such as zoom to provide a "magnified" view that allows the surgeon to identify specific tissue types and characteristics, as well as to work with increased precision.

In a typical surgical field, however, certain tissue types are difficult to identify, or tissue of interest may be at least partially obscured by other tissue. Thus, different imaging modes have proven useful for surgeons during surgery. There are systems with a single imaging mode and other systems with multiple imaging modes that provide for example visible scenes in one imaging mode and fluorescence scenes in another imaging mode.

SUMMARY

In mixed mode imaging, a unique problem was discovered when using a single-chip image capture sensor with a color filter array. The light from the surgical site is passed through color filters in a color filter array and then captured as a frame of pixel data by the single-chip image capture sensor. Unfortunately, the color filters in the color filter array allow leakage between adjacent color components in the visible spectrum and do not block wavelengths outside the visible spectrum. Thus, previous techniques used to implement mixed mode imaging do not work when a single-chip image capture sensor with a color filter array is used because imaging modes are not restricted to single color channels; all channels see a combination of the multiple image modes.

However, in one aspect, mixed mode imaging is implemented using a single-chip image capture sensor with a color filter array. The single-chip image capture sensor captures a scene of a surgical site that includes a fluorescence scene component and a visible scene component in a frame of pixel data.

In one aspect, the frame includes a first plurality of pixel data and a second plurality of pixel data, sometimes referred to as a first set of pixel data and a second set of pixel data. The first plurality of pixel data includes a first combined scene, and the second plurality of pixel data includes a second combined scene. The first combined scene, in one aspect, is a first weighted combination of a fluorescence scene component and a visible scene component due to the leakage of the color filter array. The second combined scene includes a second weighted combination of the fluorescence scene component and the visible scene component.

The surgical system also includes a scene processing module. The scene processing module extracts a plurality of display scene components from the frame of pixel data. The plurality of display scene components is presented on a display unit.

More specifically, in one aspect, the scene processing module receives the first plurality of pixel data including the first combined scene and the second plurality of pixel data including the second combined scene. A display fluorescence scene component is extracted from the first and second combined scenes, and a display visible scene component is extracted from the first and second combined scenes. The display fluorescence scene component corresponds to the fluorescence scene component, while the display visible scene component corresponds to the visible scene component. The scene processing module generates a plurality of weighted combinations of the display fluorescence scene component and the display visible scene component.

A display unit, in the surgical system, is connected to the scene processing module. The display unit receives the plurality of weighted combinations, and generates from the plurality of weighted combinations a displayed scene. The displayed scene includes a highlighted scene component corresponding to the fluorescence scene component and a reduced color scene component corresponding to the visible scene component.

The reduced color scene component combined with the fluorescence scene component provides a scene of a surgical site with pathology information and/or anatomic information highlighted for the surgeon. The highlighted fluorescence scene component identifies tissue of clinical interest. The combination of a reduced color scene component with a fluorescence scene component is one example of mixed-mode imaging.

The surgical system also includes an illuminator providing at least two illumination components. When one of the illumination components is a fluorescence excitation illumination component, other illumination components include less than all visible color components of white light. The at least two illumination components are provided at the same time. In one aspect, the illuminator includes a fluorescence excitation illumination source and a visible color component illumination source.

In one aspect, the scene processing module includes a demosaic module coupled to the image capture unit to receive, in a first color channel, the first plurality of pixel data including the first combined scene. The demosaic module demosaics the first plurality of pixel data to obtain a first plurality of image pixel data comprising the first combined scene. The demosaic module also is coupled to the image capture unit to receive, in a second color channel, the second plurality of pixel data including the second combined scene. The demosaic module demosaics the second plurality of pixel data to obtain a second plurality of image pixel data including the second combined scene.

In another aspect, the scene processing module includes a demosaic module coupled to the image capture unit to receive, in a first color channel, the first plurality of pixel data comprising the first combined scene, and to receive, in a third color channel, a third plurality of pixel data comprising a third combined scene. The demosaic module demosaics the first and third pluralities of pixel data as a single color channel to obtain a first plurality of image pixel data comprising a fourth combined scene. The demosaic module also is coupled to the image capture unit to receive, in a second color channel, the second plurality of pixel data including the second combined scene. The demosaic module demosaics the second plurality of pixel data to obtain a second plurality of image pixel data including the second combined scene.

The scene processing module also includes a scene component generator. The scene component generator receives a first plurality of image pixel data of a first color component and a second plurality of image pixel data of a second color component. The first plurality of image pixel data includes one of the first combined scene and the fourth combined scene. The second plurality of image pixel data includes the second combined scene. The scene component generator performs the extraction of the display fluorescence scene component. The display fluorescence scene component comprises a first linear weighted combination of the first plurality of image pixel data and the second plurality of image pixel data. The scene component generator also performs the extraction of the display visible scene component. The display visible scene component comprises a second linear weighted combination of the first plurality of image pixel data and the second plurality of image pixel data. The display fluorescence scene component is different from the display visible scene component. The display fluorescence scene component corresponds to the fluorescence scene component, and the display visible scene component corresponds to the visible scene component.

The surgical system performs a method including receiving a frame of pixel data captured by a single-chip image capture sensor. The single-chip image capture sensor includes a color filter array. The pixel data comprises a scene of a surgical site that includes a fluorescence scene component and a visible scene component.

In one aspect, the frame includes a first set of pixel data including a first combined scene, and a second set of pixel data including a second combined scene. The first combined scene, in one aspect, is a first weighted combination of the fluorescence scene component and the visible scene component. The second combined scene includes a second weighted combination of the fluorescence scene component and the visible scene component. The method extracts a display fluorescence scene component, a display fluorescence scene component, from the first combined scene and extracts a display visible scene component, a display visible scene component, from the second combined scene. Then, the method generates a plurality of weighted combinations of the display fluorescence scene component and the display visible scene component. Finally, the method generates from the plurality of weighted combinations a displayed scene including a highlighted fluorescence component corresponding to the fluorescence scene component and a reduced color scene component corresponding to the visible scene component.

In one aspect, the method includes illuminating a surgical site with at least two illumination components. When one of the illumination components is a fluorescence excitation illumination component, other illumination components include less than all visible color components of white light. The at least two illumination components are provided at the same time.

The method further includes demosaicing the first plurality of pixel data comprising the first combined scene to obtain a first plurality of image pixel data comprising the first combined scene. The second plurality of pixel data comprising the second combined scene is also demosaiced to obtain a second plurality of image pixel data comprising the second combined scene.

In another aspect, the method includes demosaicing the first plurality of pixel data comprising the first combined scene and a third plurality of pixel data comprising a third combined scene as a single color channel to obtain a first plurality of image pixel data comprising a fourth combined scene. In this aspect, the second plurality of pixel data comprising the second combined scene also is demosaiced to obtain a second plurality of image pixel data comprising the second combined scene.

The method still further includes receiving a first plurality of image pixel data of a first color component and a second plurality of image pixel data of a second color component. The first plurality of image pixel data comprises the first combined scene, and the second plurality of image pixel data comprises the second combined scene. The method performs the extraction of the display fluorescence scene component. The display fluorescence scene component comprises a first linear weighted combination of the first plurality of image pixel data and the second plurality of image pixel data. The method also performs the extraction of the display visible scene component. The display visible scene comprises a second linear weighted combination of the first plurality of image pixel data and the second plurality of image pixel data. The display fluorescence scene component is different from the display visible scene component. The display fluorescence scene component corresponds to the fluorescence scene component, and the display visible scene component corresponds to the visible scene component.

Figure 1:
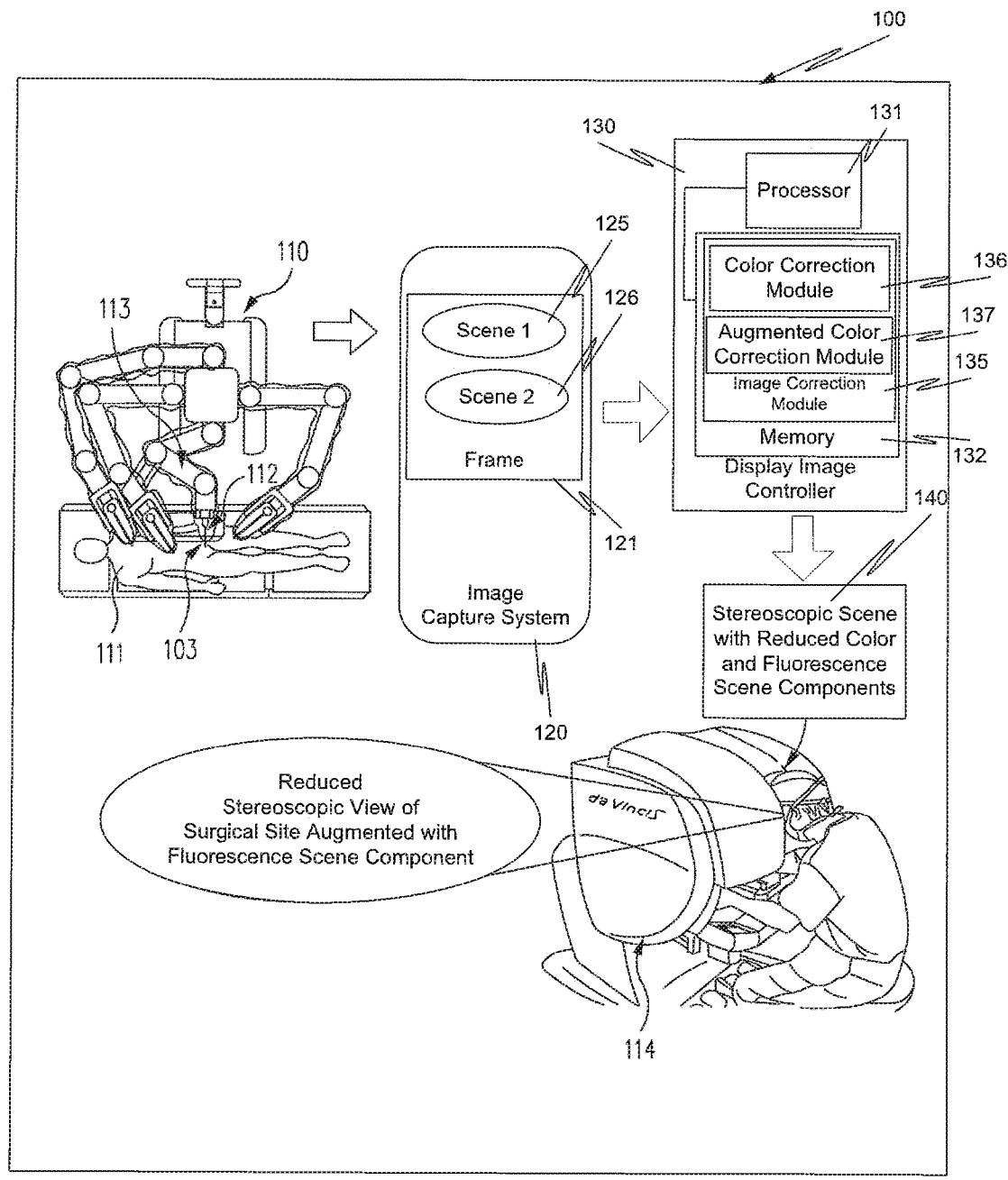
FIG. 1 is a high level diagrammatic view of a minimally invasive teleoperated surgical system including an augmented stereoscopic visualization system using a single-chip image capture sensor with a color filter array.

In the drawings, the first digit of a reference number indicates the figure in which the element with that reference number first appeared for single digit figure numbers.

DETAILED DESCRIPTION

As used herein, electronic stereoscopic imaging includes the use of two imaging channels (i.e., one channel for left side scenes and another channel for right side scenes).

As used herein, a stereoscopic endoscope includes two channels (e.g., channels for left and right images) for transporting light from an object such as tissue to be imaged. The light transported in each channel represents a different view (stereoscopic left or right) of a scene in the surgical field. Without loss of generality or applicability, the aspects described more completely below also could be used in the context of a field sequential stereo acquisition system and/or a field sequential display system.

As used herein, an illumination channel provides illumination to tissue from an illumination source located away from an image capture unit (e.g., away from the distal end of an endoscope), or an illumination source located at or near the image capture unit (e.g., one or more light emitting diodes (LEDs) at or near the distal end of an endoscope).

As used herein, scenes captured in the visible electromagnetic radiation spectrum are referred to as visible scenes.

As used herein, white light is visible white light that is made up of three (or more) visible color components, e.g., a red visible color component, a green visible color component, and a blue visible color component. If the visible color components are provided by an illuminator, the visible color components are referred to as visible color illumination components. White light may also refer to a more continuous spectrum in the visible spectrum as one might see from a heated tungsten filament or xenon lamp, for example.

As used herein, a monochromatic scene that is generated using an illuminator that provides less than all of a plurality of visible color illuminations components of white light is referred to as a reduced color scene. If the reduced color scene is a part of a scene that includes another scene component, e.g., a fluorescence scene component, the reduced color scene is referred to as a reduced color scene component.

As used herein, a visible scene component includes a visible color component.

As used herein, "first," "second," and "third" are adjectives used to distinguish between color components. Thus, "first," "second," and "third" are not intended to imply any ordering of the color components within the visible wavelength spectrum.

As used herein, a single-chip image capture sensor includes a single integral semiconductor device on which all the color components in white light are captured. The photosensors on the chip detect light intensity with little or no wavelength specificity. Thus, the single-chip image capture sensor also includes a color filter array. The color filter array filters the incoming light by wavelength range so that different sets of photosensors capture different color components.

As used herein, pixels refer to photosensors on the single-chip image capture sensor. The pixels capture pixel data. A set of pixel data captured for a color component is interpolated, referred to herein as demosaiced, to generate a plurality of image pixel data for that color component. Thus, a pixel and an image pixel, as used herein, are different entities.

As used herein, scene components captured by an image capture sensor as the result of fluorescence are referred to as acquired fluorescence scene components, and sometimes simply as fluorescence scene components. There are various fluorescence imaging modalities. Fluorescence may result from natural tissue fluorescence, or the use of, for example, injectable dyes, fluorescent proteins, or fluorescent tagged antibodies. Fluorescence may result from, for example, excitation by laser or other energy source. In such configurations, it is understood that a notch filter is used to block the excitation wavelength that enters the endoscope. Fluorescence scene components can provide vital in vivo patient information that is critical for surgery, such as pathology information (e.g., fluorescing tumors) or anatomic information (e.g., fluorescing tagged tendons).

Aspects of this invention augment the stereoscopic video capturing and viewing capability of a minimally invasive surgical system, e.g., the da Vinci® minimally invasive teleoperated surgical system commercialized by Intuitive Surgical, Inc. of Sunnyvale, Calif., by incorporating both stereoscopic normal visible scenes, and alternatively stereoscopic reduced color scene components combined with fluorescence scene components. (da Vinci® is a registered trademark of Intuitive Surgical Operations, Inc. of Sunnyvale, Calif.) A stereoscopic reduced color scene component combined with a fluorescence scene component provides a stereoscopic image of a surgical site with pathology information and/or anatomic information highlighted for the surgeon. The highlighted fluorescence scene component identifies tissue of clinical interest. The combination of a reduced color scene component with a fluorescence scene component is one example of mixed-mode imaging.

The stereoscopic reduced color scene component combined with the fluorescence scene component is provided in real time to a surgeon performing a surgical operation using a minimally invasive teleoperated surgical system. A minimally invasive teleoperated surgical system is an example of a robotic surgical system. Sequential acquisition approaches (also known as time slicing) incur a delay associated with capturing a stereoscopic image in one frame and the fluorescence image in another frame and then using the two frames taken at different points in time to generate a single frame that is displayed for the surgeon. Hence, the memory and processing requirements of the system described herein are reduced with respect to systems that utilize time slicing to superimpose a fluorescence scene component on a stereoscopic color visible scene component.

The stereoscopic reduced color scene component is formed using an illuminator that provides less than all the plurality of visible color illumination components that make white light and so color information in the reduced color scene component is lost but there is little or no loss in detail. The stereoscopic reduced color scene component is sufficient to identify anatomy, tissue landmarks, and surgical instruments so that this image allows safe manipulation of the surgical instruments. With the reduced color scene component, there is no loss in contrast of the fluorescence scene component due to interference by a visible color illumination component.

In one aspect, the fluorescence scene component is overlaid onto the reduced color scene component and color enhanced to provide improved information content regarding the surgical site that reduces the risk of injury to the patient and that improves surgical efficiency. This combination of a stereoscopic reduced color scene component and a highlighted fluorescence scene component provides benefits including, but not limited to, allowing a surgeon in real-time to identify positive tumor margins for diseased tissue excision and to identify other tissue, e.g., tendons, so as to avoid unnecessarily cutting that tissue.

The combination of the reduced color scene components and the fluorescence scene components may be continuously displayed to the surgeon. Alternatively, the overlay of the two scene components may be toggled on and off (e.g., by using a foot pedal or by double-clicking master finger grips on the da Vinci® Surgical System surgeon's console).

Herein, an example of mixed mode imaging is simultaneously displaying both a reduced color scene of a white-light scene and a fluorescence scene that are optically aligned. Typically, the reduced color scene is required to carry out surgery while the fluorescence scene helps a surgeon to locate blood vessels and cancer tissues and margins, as indicated above.

Mixed imaging modes, sometimes referred to as augmented modes, are of great interest to a surgeon since the surgeon can carry out the complete cycle of diagnostics, surgery, and monitoring on the fly. It is quite common that one color camera and one near infrared camera are integrated to operate under such modes.

To reduce the integration complexity associated with the integration of two cameras, an image capture system based on a three-chip sensor has been used for mixed mode imaging. With the three-chip sensor, for example, green illumination, blue illumination, and near infrared laser illumination are simultaneously used to obtain a black and white version of a white image from the green and blue color channels and a fluorescence scene from the red color channel. Unfortunately, this is not a solution for an inexpensive single-chip image capture sensor, as described more completely below.

There are other possible solutions to mixed mode imaging such as the sequential (color or wavelength) imaging systems with a mono-chrome sensor and tunable illuminations. The main issue of these sequential imaging systems is the motion-induced color fringe between images taken at different times under different illuminations.

In mixed mode imaging using a single-chip image capture sensor with a color filter array to capture information, the light from the surgical site is passed through filters in the color filter array and then captured as pixel data by the single-chip image capture sensor. Each filter in the color filter array is a band pass filter. A band pass filter passes light having wavelengths within a certain range and blocks passage of wavelengths outside that range. Thus, the component of the light, i.e., the wavelengths of light, from surgical site captured by a pixel is determined by the color of the filter for that pixel in the color filter array.

Many different types of color filter arrays are known. A commonly used color filter array is a Bayer color filter array. The Bayer color filter array has three different color filters. For example, with a color model that has red, green, and blue color components, the Bayer color filter array has red filters, blue filters, and green filters. As noted above, each filter is a bandpass filter. A green filter passes green light and blocks red and blue light. Thus, a pixel with a green filter captures green light. A pixel with a red filter captures red light, and a pixel with a blue filter captures blue light.

Typically, the bandpass filters are made using dyes. The dyes work reasonably well in the visible spectrum, but do not block light that is outside the visible spectrum. For example, if fluorescence is in the infrared spectrum, the fluorescence passes through each of the red, green, and blue filters and is captured by the corresponding pixels. Thus, if green color component illumination in conjunction with fluorescence excitation illumination that excites fluorescence in the infrared spectrum is used, the red and blue pixels capture the fluorescence, while the green pixel captures a combination of the reflected green light and the fluorescence.

Also, typically there is some leakage of adjacent visible color components though a filter in the Bayer filter array. Thus, a green pixel may capture some red light and some blue light in addition to the green light. A red pixel may capture some green light in addition to the red light, and a blue pixel may capture some green light in addition to the blue light.

Thus, in the augmented mode, when green light illumination is used in conjunction with florescence excitation illumination that excites infrared fluorescence, the surgical site scene includes reflected green light, which is an example of a visible scene component, and fluorescence, which is a fluorescence scene component. Each of the red, green and blue color filters in the color filter array passes the fluorescence so that all pixels capture the fluorescence scene component. The red color filter also passes a portion of the reflected green light, sometimes referred to as leakage, and so the pixels associated with the red color filter capture a first combination of a portion of the reflected green light and the fluorescence. The green color filter passes the reflected green light and so the pixels associated with the green color filter capture a second combination of the reflected green light and the fluorescence. The blue color filter also passes a portion of the reflected green light and so the pixels associated with the blue color filter capture a third combination of a portion of the reflected green light and the fluorescence.

In more general terms, the pixels for a first color component capture a combined scene that is a first weighted combination of the fluorescence scene component and a visible color component scene component. The pixels for a second color component capture a combined scene that is a second weighted combination of the fluorescence scene component and a visible color component scene. The pixels for a third color component capture a combined scene that is a third weighted combination of the fluorescence scene component and a visible color component scene. Here, weighted combination is used to convey the concept that the light captured by a set of pixels is a combination of the visible color component scene and the fluorescence scene component and the particular weighted combination is determined by the characteristics of the color filter for a color component.

As described more completely below, mixed mode imaging is implemented using a single-chip image capture sensor that includes a color filter array. The characteristics of the color filter array, as described above, and the resulting light that is captured are taken into account, and a plurality of display scene components are extracted from the captured pixel data and presented on a display unit. In the following description, a fluorescence scene component is used as an example of a first scene component, and a visible color component scene is used as an example of a second scene component. In this example, a combined scene is a combination of the first scene component and the second scene component. As described above, a first set of pixels in the single-chip image capture sensor captures the first combined scene, and a second set of pixels in the single-chip image capture sensor captures the second combined scene. The pixel data is captured in the same frame as opposed to in two different frames in the previous sequential processing techniques.

Also, in the following examples, fluorescence excitation illumination is used simultaneously with a single visible color illumination component. The fluorescence excitation illumination excites fluorescence having wavelengths outside the visible spectrum.

The use of a single visible color illumination component also is illustrative and is not intended to be limiting. The aspects described more completely below work with illumination that includes less than all the color components of white light. Also, the fluorescence does not have to be outside the visible spectrum. For example, if green illumination is used, and the fluorescence is in the blue spectrum such that some of the fluorescence leaks through the green color filter, the following aspects are applicable.

FIG. 1 is a high level diagrammatic view of a minimally-invasive teleoperated surgical system 100, for example, the da Vinci® Surgical System, including a stereoscopic visualization system. In this example, a surgeon, using a surgeon's console 114, remotely manipulates an endoscope 112 mounted on a robotic manipulator arm 113 that in turn is mounted on cart 110. There are other parts, cables etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 23, 2007; disclosing Minimally Invasive Surgical System), U.S. Pat. No. 6,837,883 B2 (filed Oct. 5, 2001; disclosing Arm Cart for Telerobotic Surgical System), and U.S. Pat. No. 6,331,181 (filed Dec. 28, 2001; disclosing Surgical Robotic Tools, Data Architecture, and Use), all of which are incorporated herein by reference.

As explained more completely below, an illumination system (not shown), sometimes referred to as an illuminator, is coupled to endoscope 112. In one aspect, the illumination system selectively provides one of (a) white light illumination and (b) less than all the visible color illumination components of white light and at least one fluorescence excitation illumination component. The light from the illumination system is coupled to at least one illumination channel in endoscope 112, in one aspect. The light passes through at least one illumination channel in endoscope 112 and illuminates tissue 103 of a patient 111.

Endoscope 112 also includes, in one aspect, two stereoscopic optical channels, e.g., a left optical channel and a right optical channel, for passing light from the tissue, e.g., reflected white light or the reflected light from the visible color illumination component(s) and fluorescence. The white light reflected from tissue 103 is captured as a normal acquired visible color stereoscopic scene by image capture system 120. However, when the surgeon wants to see an augmented scene, the surgeon changes the viewing mode to an augmented viewing mode.

In the augmented viewing mode, the illumination source provides less than all of the visible color illumination components of white light. For example, if three visible color illumination components of white light are used, at most two visible color illumination components are provided by the illumination source. Thus, in this aspect of the augmented viewing mode, tissue 103 is illuminated with one or two visible color illumination components, e.g., with less than all the plurality of visible color illumination components of white light, and a fluorescence excitation illumination component.

Each of the left and right channels in image capture system 120 includes a single-chip image capture sensor with a color filter array. Thus, in the augmented viewing mode when tissue 103 is illuminated with one or two visible color illumination components and a fluorescence excitation illumination component, each image capture unit captures a scene of a surgical site that includes a fluorescence scene component and a visible scene component in a frame of pixel data. A first plurality of pixels captures a first combined scene 125 in a frame 121, e.g., captures a first combined scene including a first weighted combination of the fluorescence scene component and the visible color component scene. A second plurality of pixels captures a second combined scene 126 in frame 121, e.g., captures a second combined scene including a second weighted combination of the fluorescence scene component and the visible color component scene.

In more general terms, the single-chip image capture sensor with a color filter array includes a first plurality of pixels that captures a first combined scene 125 in a frame of pixel data 121. First combined scene 125 is a first weighted combination of a first scene component of the surgical site and a second scene component of the surgical site. The single-chip image capture sensor also includes a second plurality of pixels that capture a second combined scene 126 in frame 121. Second combined scene 126 is a second weighted combination of the first scene component of the surgical site and the second scene component of the surgical site. The second scene component is different from the first scene component. Also, the first weighted combination is different from the second weighted combination.

In this aspect, image capture system 120 is a conventional single-chip image capture system with a color filter array except any filter or filters that would block the fluorescence are removed. A filter or filters may be used to block capture of any direct light or reflected light from the fluorescence excitation source or sources.

Display image controller 130 receives the acquired pixel data from image capture system 120. When the acquired pixel data is normal visible color stereoscopic scenes, a color correction module 136 in an image correction module 135 of display image controller 130 processes the acquired pixel data including color correction to generate color corrected visible full color stereoscopic scenes. The color corrected visible full color stereoscopic scenes are sent to the stereoscopic viewer on surgeon's console 114, which displays the stereoscopic scenes.

Similarly, in the augmented viewing mode, display image controller 130 receives the acquired pixel data from image capture system 120. For example, for a three-component color space, if the illumination source provides one visible color illumination component i.e., a first visible color illumination component, and a fluorescence excitation illumination component, three sets of pixel data are acquired. A first set of the acquired pixel data is a first combined scene that includes a first weighted combination of the acquired visible color component scene and the acquired fluorescence scene component. A second set of the acquired pixel data is a second combined scene that includes a second weighted combination of the acquired visible color component scene and the acquired fluorescence scene component. A third set of acquired pixel data is a third combined scene that includes a third weighted combination of the acquired visible color component scene and the acquired fluorescence scene component. Display image controller 130 receives the three sets of acquired pixel data that are in a single frame.

In the augmented viewing mode, an augmented color correction module 137 in image correction module 135 of display image controller 130 uses an augmented color correction process to process the acquired pixel data in each of the left and right channels of image capture system 120. The augmented image correction process generates a display visible color scene component and a display fluorescence scene component in each of the left and right channels.

In one aspect, the augmented color correction module in display image controller 130, as explained more completely below, provides a linear weighted combination of the display visible component scene and the display fluorescence scene component to each color channel of the display unit in surgeon's console 114. The display unit displays a display scene that includes a reduced color scene component and a fluorescence scene component. The fluorescence scene component is highlighted on the display unit because pixels for a color component in the display that receive a part of the fluorescence scene component also receive a part of the reduced color scene component are so are brighter relative to neighboring pixels of the reduced color scene component that receive only a part of the reduced color scene component.

Figure 2:
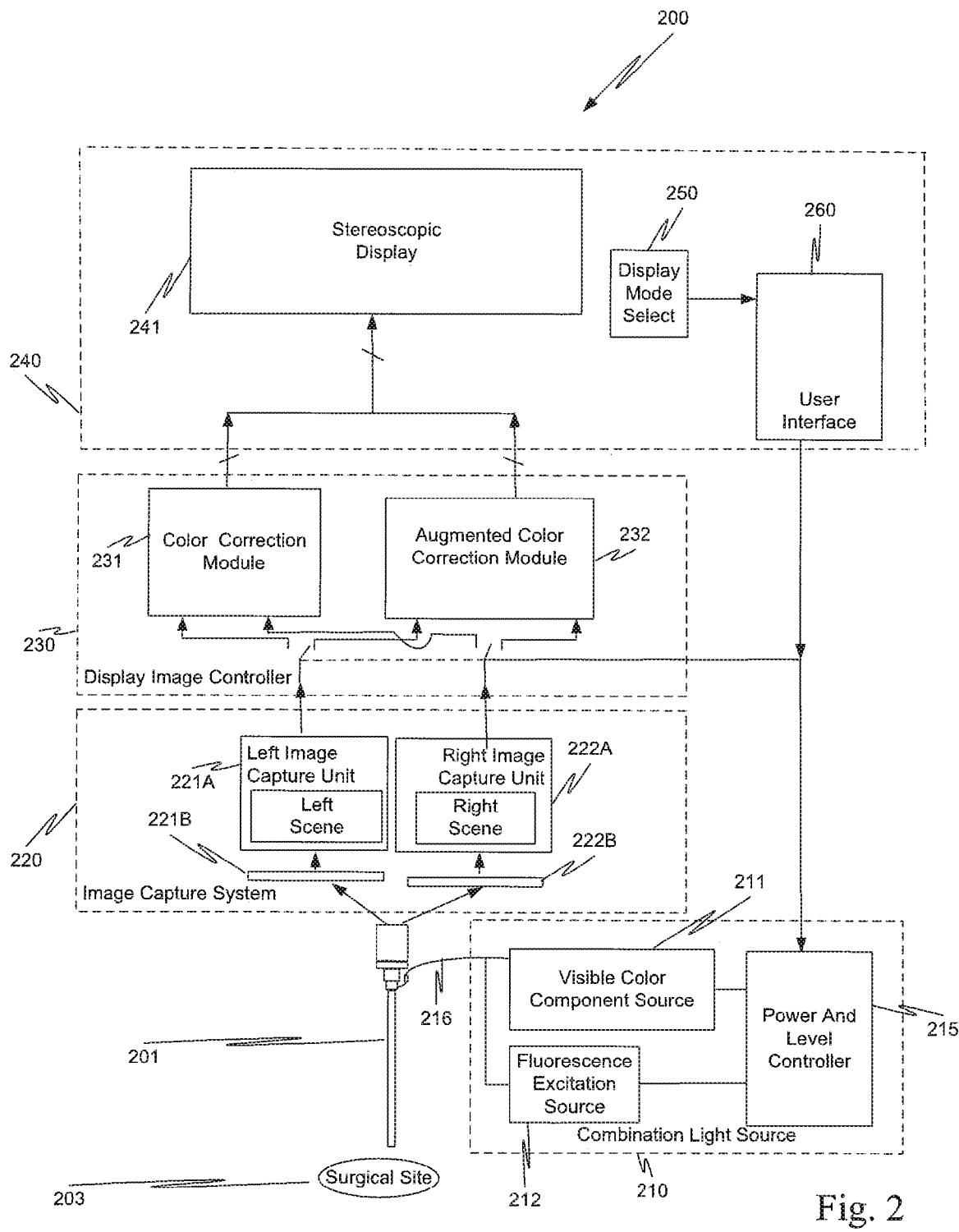
FIG. 2 is a schematic view that illustrates hardware and software (image processing and user interface) aspects of augmented stereoscopic visualization system.
Figure 3:
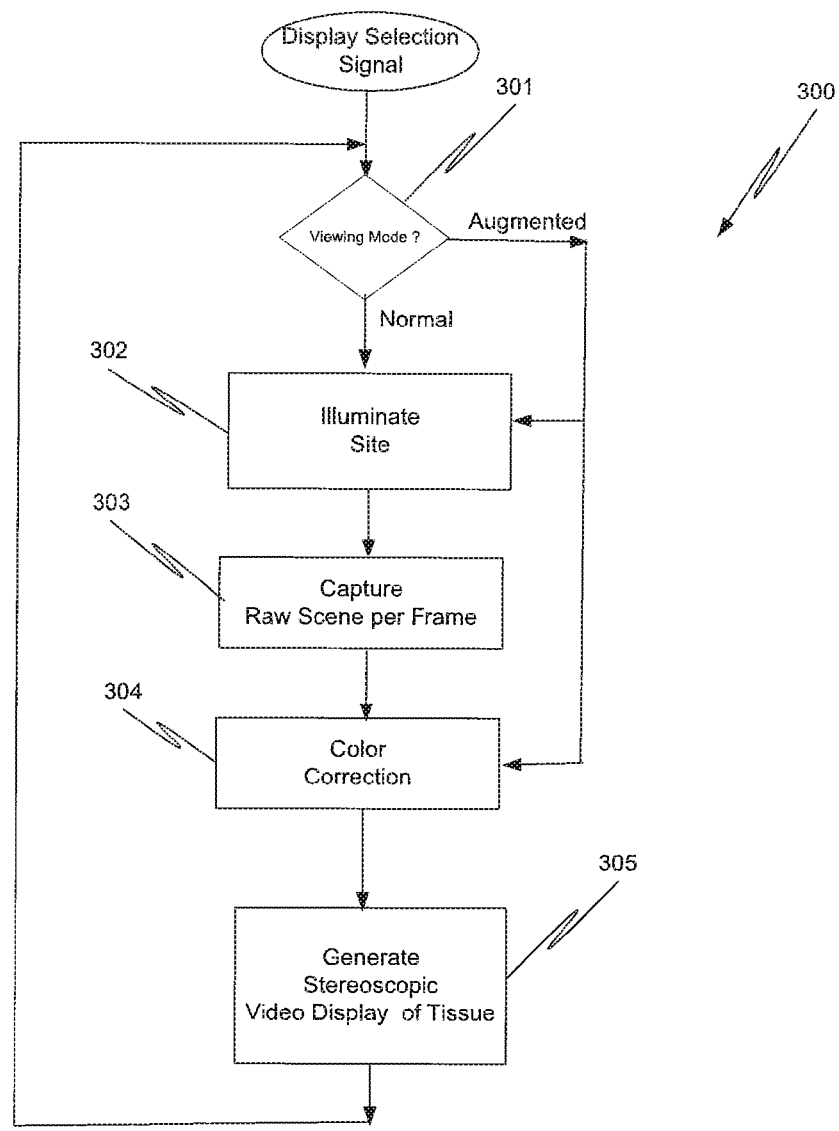
FIG. 3 is process flow diagram of a process performed using, for example, the augmented stereoscopic visualization system of the minimally invasive teleoperated surgical system of FIG. 1.
Figure 4:
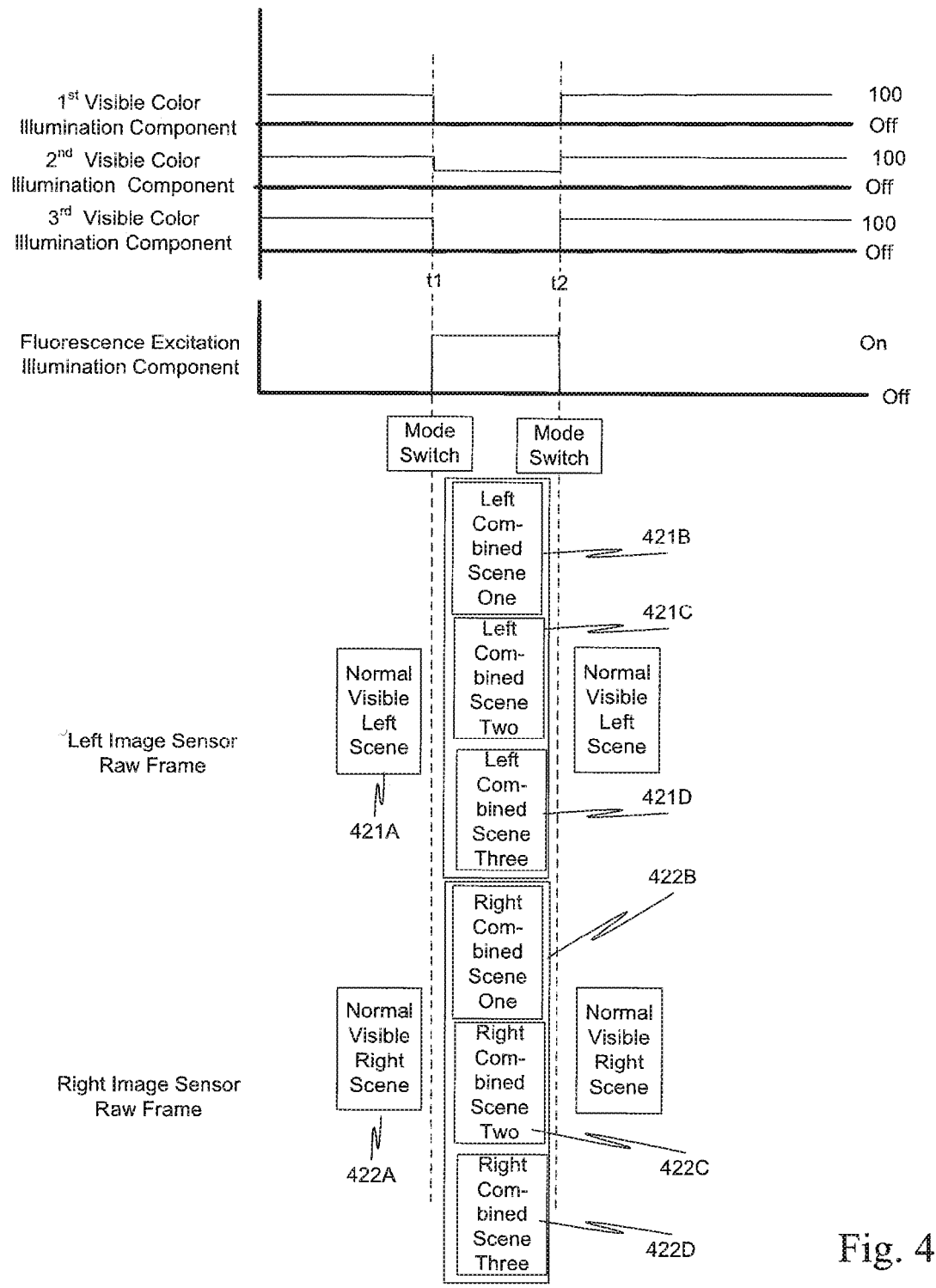
FIG. 4 illustrates one aspect of the timing, synchronization, and capture of frames in the system in FIGS. 2 and 3.

FIG. 2 is a more detailed illustration of the aspects of one example of minimally invasive surgical system 100 of FIG. 1. FIG. 3 is a high-level process flow diagram for the operation of the system in FIG. 2, while FIG. 4 is a timing diagram for the illumination of a surgical site and the capture of frames in the system of FIG. 2.

In the embodiment of FIG. 2, minimally invasive surgical system 200 includes an illuminator that is combination light source 210. Combination light source 210 includes a visible color component source 211 and a fluorescence excitation source 212, in this aspect. The particular implementation of sources 211 and 212 is not critical so long as combination light source 210 has the capabilities described more completely below.

Combination light source 210 is used in conjunction with at least one illumination channel in a stereoscopic endoscope 201 to illuminate surgical site 203 in an ILLUMINATE TISSUE process 302 (FIG. 3). In this example, combination light source 210 has two modes of operation: a normal viewing mode and an augmented viewing mode.

In the normal viewing mode, visible color component source 211 provides illumination that illuminates surgical site 203 in white light, i.e., all the visible color component illumination sources in source 211 are used. Fluorescence excitation source 212 is not used in the normal viewing mode.

In the augmented viewing mode, visible color component source 211 provides less than all the visible color components needed to illuminate surgical site 203 in white light, e.g., one or more of the visible color components of white light are not included in the illumination. In some aspects, for example, it may be possible to use all the visible color illumination components of white light in the augmented viewing mode, but include trivial illumination from one or more of the visible color illumination components and augmented viewing mode illumination from the remaining visible color illumination component or components. Trivial illumination means that the illumination provided by the visible color component illumination source is so low that when reflected light from the trivial illumination and florescence are acquired together, the acquired trivial illumination data does not degrade the acquired fluorescence data. Thus, providing trivial illumination for the one or more visible color illumination components is effectively the same as illuminating the tissue with less than all the visible color components of white light.

In one aspect, three visible color components make up white light illumination, i.e., white light includes a first visible color component C1, a second visible color component C2, and a third visible color component C3. Each of the three visible color components C1, C2, C3 is a different visible color component, e.g., a red component, a green component, and a blue component. The use of three visible color components C1, C2, C3 to make up white light illumination is illustrative of a plurality of such components and is not intended to be limiting.

In the augmented viewing mode, fluorescence excitation source 212 provides a fluorescence excitation illumination component that excites fluorescence from surgical site 203. For example, narrow band light from fluorescence excitation source 212 is used to excite tissue-specific fluorophores so that fluorescence scenes of specific tissue within surgical site 203 are captured.

In the augmented viewing mode, the number of visible color illumination components provided by visible color component source 211 depends on: the number of different fluorescence scene components captured; and the number of color components used to make white light. In one aspect, where three visible color illumination components C1, C2, C3 are used to make white light and a single-chip image capture sensor with a color filter array is used in each of the left and right channels of image capture system 220, one visible color illumination component is provided by visible color component source 211 and fluorescence excitation source 212 provides fluorescence excitation illumination.

In one aspect, visible color component source 211 includes a source for each of the different visible color illumination components in the plurality of visible color illumination components of white light. For a red-green-blue implementation, in one example, the sources are light emitting diodes (LEDs), a red LED, two green LEDs and a blue LED. Table 1 gives the range of output wavelengths for each of the LEDs used in this example.

TABLE 1

| Visible Color Illumination Component | Wavelength |
|---|---|
| Red | 670 nanometers (nm) |
| Green 1 | 555 nm |

TABLE 1-continued

| Visible Color Illumination Component | Wavelength |
|---|---|
| Green 2 | 532 nm |
| Blue | 450 nm |

The use of LEDs in visible color component source 211 is illustrative only and is not intended to be limiting. Visible color component source 211 could also be implemented with multiple laser sources instead of LEDs for example. Alternatively, visible color component source 211 could use a Xenon lamp with an elliptic back reflector and a band pass filter coating to create broadband white illumination light for visible images. The use of a Xenon lamp also is illustrative only and is not intended to be limiting. For example, a high pressure mercury arc lamp, other arc lamps, or other broadband light sources may be used. To eliminate one or more visible color illumination components from such a source in the augmented viewing mode, bandpass filters, prisms etc. could be incorporated in combination light source 210.

The use of a light source that is removed from endoscope 201 is also illustrative and not intended to be limiting. In some aspects, the light source could be mounted on the distal end of endoscope 201, for example.

Also, in the augmented viewing mode for a fluorescence excitation wavelength occurs outside the visible spectrum (e.g., in the near infrared (NIR)), a laser module (or other energy source, such as a light-emitting diode or filtered white light) is used as fluorescence excitation source 212. Thus, in one aspect, fluorescence is triggered by light from a laser module in fluorescence excitation source 212. For example, the FDA approved fluorescent dye Indocyanine Green has an excitation maximum of 810 nm and an emission maximum of 830 nm.

In either the normal or augmented viewing modes, the light from the light source or light sources is directed into an illumination channel 216. Illumination channel 216 provides the light to another illumination channel in stereoscopic endoscope 201 that in turn directs the light to surgical site 203.

The video output on stereoscopic display unit 241 may be toggled between the normal and augmented viewing modes by using, e.g., a foot switch, a double click of the master grips that control the surgical instruments, voice control, and other like switching methods. The toggle for switching between the two viewing modes is represented in FIG. 2 as display mode select unit 250.

In response to a user input from display mode select unit 250, a signal is provided to a VIEWING MODE check process 301 (FIG. 3) in a user interface 260 that in turn provides a control signal to ILLUMINATE TISSUE process 302 when the normal viewing mode is selected. User interface 260, in one aspect, is generated by computer code, which is stored in a memory 132, executing on a processor 131 (FIG. 1).

In one aspect, the normal viewing mode is a default mode. In this aspect, display mode select unit 250 would not be used until the surgeon wanted to change the viewing mode from the normal viewing mode to the augmented viewing mode or from the augmented viewing mode to the normal viewing mode.

In the normal viewing mode, ILLUMINATE TISSUE process 302 sends a normal viewing mode operation signal to power and level controller 215 in combination light source 210. Power and level controller 215 is illustrated in combination light source 210 for convenience and is not intended to limit the location of power and level controller 215 to this specific location.

In response to the normal viewing mode operation signal, power and level controller 215 turns off fluorescence excitation source 212, if source 212 is on, and enables visible color component source 211 so that white light is provided to surgical site 203. For example, when visible color component source 211 includes three visible color illumination component sources, power is provided to each of the three sources. Those knowledgeable in the field recognize that instead of turning the power on and off to the various sources in 210, controller 215 could maintain the power always on and direct the output from the sources to and away from channel 216 and achieve the same result.

Thus, in the normal viewing mode, ILLUMINATE TISSUE process 302 causes surgical site 203 to be illuminated with white light. In the graphs of the illumination in FIG. 4, the horizontal axis is time and the vertical axis represents source output level. The source output level during normal viewing mode operation for each of the three visible color illumination components is defined as 100 percent. Thus, in FIG. 4 for times before time t1, the output level from each of the three visible color illumination components is shown as 100 percent and the output level for the fluorescence excitation illumination component is zero.

The visible light from surgical site 203 (FIG. 2) is passed by the stereoscopic optical channels in endoscope 201 to image capture system 220. Image capture system 220, in this aspect, includes a stereoscopic image capture system that includes a left image capture unit 221A that is a first single-chip image capture sensor with a color filter array and a right image capture unit 222A that is a second single-chip image capture sensor with a color filter array.

Thus, in CAPTURE RAW SCENE PER FRAME process 303 (FIG. 3) in the normal viewing mode, left image capture unit 221A captures a visible left scene 421A (FIG. 4) in a frame and right image capture unit 222A captures a visible right scene 422A in a frame. Left image capture unit 221A captures red, green, and blue pixel data for visible left scene 421A, i.e., the acquired left scene is a color scene. Similarly, right image capture unit 222A captures red, green, and blue pixel data for visible right image 422A.

In the normal viewing mode, acquired normal left visible scene 421A and acquired normal visible right scene 422A (FIG. 4) are provided to display image controller 230 (FIG. 2) that performs COLOR CORRECTION process 304 (FIG. 3). When the augmented signal is false, i.e., in the normal viewing mode, display image controller 230 couples the acquired scenes in image capture system 220 to color correction module 231. Thus, in COLOR CORRECTION process 304, color correction module 231 processes both acquired normal left visible scene 421A and acquired normal right visible scene 422A. The color corrected acquired normal left visible scene and the color corrected acquired normal right visible are sent to stereoscopic display unit 241 and a stereoscopic full color scene is displayed in GENERATE A STEREOSCOPIC VIDEO DISPLAY OF TISSUE process 305.

The processing in the normal viewing mode is equivalent to the processing in a conventional minimally invasive surgical system and so is known to those knowledgeable in the field. Also, processes 301 to 305 are performed repetitively for each frame so that the surgeon sees a real-time video image of surgical site 203.

Figure 6A:
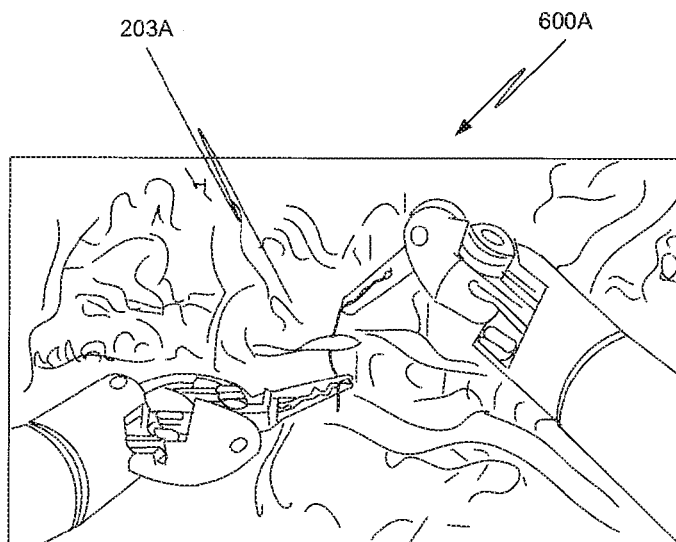
FIG. 6A is a representation of a normal color stereoscopic image obtained using the system of FIG. 2.

During the normal viewing mode, the surgeon is provided with a normal three-dimensional color view 600A of surgical site 203A (FIG. 6A). However, the surgeon may wish to see a region or regions of interest in surgical site 203A highlighted in the three-dimensional view of surgical site 203A. For example, the surgeon may which to see diseased portions of surgical site 203A and/or a specific tissue, e.g., a tendon or organ. Thus, at time t1 (FIG. 4), the surgeon uses display mode select unit 250 to change the viewing mode to the augmented viewing mode.

In response to the user input from display mode select unit 250, an augmented display selection signal is provided to a VIEWING MODE check process 301 in user interface 260. In response to the augmented display selection signal, check process 301 provides an augmented imaging control signal to ILLUMINATE TISSUE process 302 and to COLOR CORRECTION process 304.

In response to the augmented display control signal, ILLUMINATE TISSUE process 302 sends an augmented display signal having a state of true to power and level controller 215 in combination light source 210. In response to the augmented display signal having state true, power and level controller 215 turns on fluorescence excitation source 212 and in this example turns off the first and third visual color illumination components in visible color component source 211 so that only the second visual color illumination component and the fluorescence excitation illumination component are supplied to illumination channel 216. Thus, surgical site 203 is illuminated with the second visual color illumination component, but not with the first and third visual color illumination components. Surgical site 203 is also illuminated with the fluorescence excitation illumination component.

Also, in one embodiment, power and level controller 215 reduces the output level of the second visual color illumination component, e.g., reduces the output level to one part in ten. Thus, as shown in FIG. 4, after time t1, the output level of the second visual color illumination component is reduced relative to the output level prior to time t1, and the first and third visual color component illumination output levels are zero. Also, the fluorescence excitation illumination component is turned on. As explained more completely below, the output level is reduced to avoid saturation of pixels and to maintain a proper contrast between the acquired visible scene component or components and the acquired fluorescence scene component.

The light from surgical site 203 (FIG. 2) is passed by the stereoscopic left and right optical channels in endoscope 201 to image capture system 220. In one aspect, filters 221B, 222B are used to filter any reflected or direct light from fluorescence excitation source 212 before the scenes are captured.

Prior to considering CAPTURE RAW SCENE PER FRAME process 303 (FIG. 3), a single-chip image capture sensor with a color filter array is briefly considered. Many different types of color filter arrays are known. A commonly used color filter array is a Bayer color filter array. For a three visible color component color space (C1, C2, C3), a Bayer color filter array has about twice as many filters for one visible color component as for each of the other two color components. For example, in a six by six pixel block, one implementation of the Bayer color filter array has eighteen filters for color component C2, nine filters for color component C1, and nine filters for color component C3. The layout of the color filters in the Bayer pattern is well known and so is not described further herein.

The use of a three color component Bayer filter is illustrative only and is not intended to be limiting. Other types of color filter arrays can be used such as, for example, a red-green-blue-emerald color filter array.

In capture RAW SCENE PER FRAME process 303 (FIG. 3), in the augmented viewing mode, left image capture unit 221A captures a frame that includes a plurality of sets of pixel data. Each set of pixel data can also include captured light from colors components in the visible spectrum adjacent to the color of the color filter. This captured light leaked through the color filter for that set of pixels. In this example, the visible color component illumination is for the second color component.

Thus, in left image capture unit 221A, a first set of pixel data for first color component C1 is a first combined scene 421B (FIG. 4) that is a first weighted combination of a left visible second color component scene, i.e., the reflected second color component illumination that leaked through the first color component filter, and a left fluorescence scene component. A second set of pixel data for second color component C2 is a second combined scene 421C (FIG. 4) that is a second weighted combination of the left visible second color component scene and the left fluorescence scene component. A third set of pixel data for a third color component C3 is a third combined scene 421D (FIG. 4) that is a third weighted combination of a left visible second color component scene, i.e., the reflected second color component illumination that leaked through the third color component filter, and a left fluorescence scene component. Note that the weights in each of the combined scenes are determined by the characteristics of the filter in the color filter array for that color component.

Right image capture unit 222A also captures a frame that includes a plurality of sets of pixel data. Again, each set of pixel data can also include captured light from colors components in the visible spectrum adjacent to the color of the color filter. This captured light leaked through the color filter for that set of pixels. In this example, the visible color component illumination is second color component illumination.

Thus, in right image capture unit 222A, a first set of pixel data for first color component C1 is a first combined scene 422B (FIG. 4) that is a first weighted combination of a right visible second color component scene, i.e., the reflected second color component illumination that leaked through the first color component filter, and a right fluorescence scene component. A second set of pixel data for second color component C2 is a second combined scene 422C (FIG. 4) that is a second weighted combination of the right visible second color component scene and the right fluorescence scene component. A third set of pixel data for a third color component C3 is a third combined scene 422D (FIG. 4) that is a third weighted combination of the right visible second color component scene, i.e., the reflected second color component illumination that leaked through the third color component filter, and a right fluorescence scene component. As noted above, the weights in each of the combined scenes are determined by the characteristics of the filter in the color filter array for that color component.

No additional cameras, optic channels in the endoscope, or additional endoscopes are needed to acquire both the visible color component scene and the fluorescence scene component. Herein, when it is stated that a visible color component scene in a scene is associated with a visible color component illumination source, it means that the visible color component illumination source provides the light that results in that visible color component scene in the image.

Recall, as described above, display scene controller 230 has received the augmented display signal having state true.

Thus, display scene controller 230 changes from color image correction module 231 to augmented color correction module 232. In the augmented viewing mode, the acquired raw scene data is provided to augmented color correction module 232 that performs COLOR CORRECTION process 304. Hence, in one aspect, COLOR CORRECTION process 304 is used in both color image correction module 231 and augmented color correction module 232. The processing performed by COLOR CORRECTION process 304 depends on the module that is using COLOR CORRECTION process 304.

Figure 5:
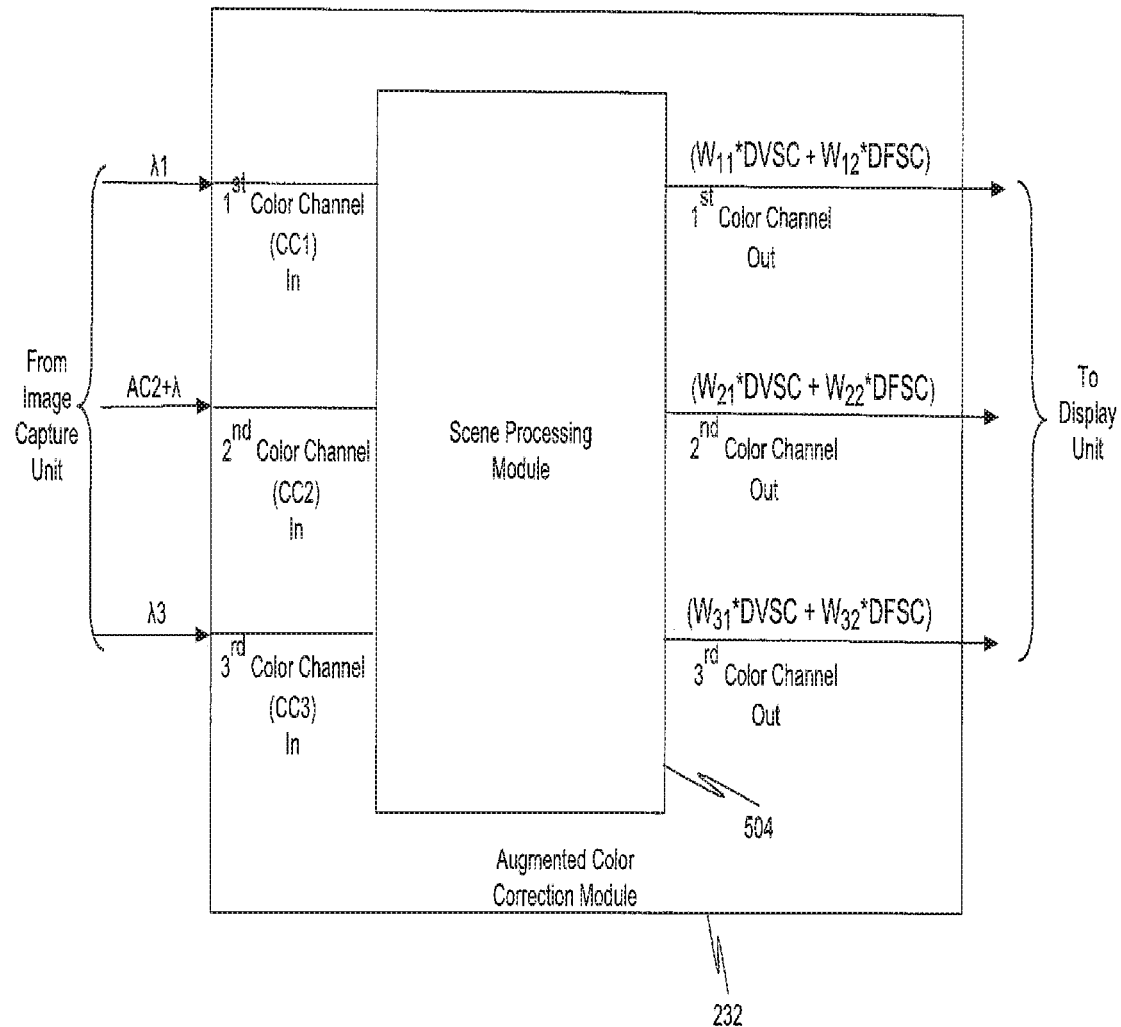
FIG. 5 is a more detailed block diagram of the augmented color correction module of FIG. 2.

COLOR CORRECTION process 304, as implemented by augmented color correction module 232, performs the same process on both the left and right acquired pixel data, and so the left and right designation is not considered in the description. FIG. 5 is a block diagram of the input information to augmented color correction module 232, and the output information from augmented color correction module 232.

A scene processing module 504 in augmented color correction module 232 performs an augmented color correction process as process 304. The augmented color correction process receives on a first input color channel CC1 the acquired pixel data including first combined scene λ1 that includes fluorescence scene component λ, on a second input color channel CC2 acquired pixel data including the second combined scene of second visible color component scene AC2 and fluorescence scene component λ, and on a third input color channel CC3 acquired pixel data including third combined scene λ3 that includes fluorescence scene component λ. The augmented color correction process scales the color channel inputs to compensate for any differences in the responses of the color filters in the color filter array to the fluorescence.

Next, the augmented color correction process, as explained more completely below, demosaics the acquired pixel data to generate a full resolution array of image pixel data for at least two of the three color components—a first full resolution array of image pixel data for first color component C1 includes first combined scene λ1 that includes fluorescence scene component λ. A second full resolution array of image pixel data for the second color component C2 includes the second combined scene that includes acquired second visible color component scene AC2 combined with acquired fluorescence scene component λ. A third full resolution array of image pixel data for third color component C3 includes third combined scene λ3 that includes fluorescence scene component λ.

Scene processing module 504 generates a display visible scene component DVSC by using the first full resolution array of image pixel data including fluorescence scene component λ to remove the contribution of fluorescence scene component λ from the second full resolution array of image pixel data. More specifically, scene processing module 504 generates display visible scene component DVSC using a weighted linear combination of the image pixel data in the first and second full resolution arrays of image pixel data. Scene processing module 504 also generates a display fluorescence scene component DFSC using a weighted linear combination of the image pixel data in the first and second full resolution arrays.

Finally, scene processing module 504 generates a weighted combination of display visible scene component DVSC and display fluorescence scene component DFSC for each input color channel of stereoscopic display unit 241. In the example of FIG. 5, stereoscopic display unit 241 has three input color channels. Thus, scene processing module 504 outputs three visible color channel inputs which are weighted combinations of display visible scene component DVSC and display fluorescence scene component DFSC. In FIG. 5, the weights are $W_{11}$, $W_{12}$, $W_{21}$, $W_{22}$, $W_{31}$, and $W_{32}$.

Consider the example, where $W_{11}=W_{21}=W_{31}=W_{22}=1$ and $W_{12}=W_{32}=0$, augmented color correction module 232, in this example, adds display fluorescence scene component DFSC to display visible scene component DVSC. The result of the addition is supplied to the second output color channel. In this example, display visible scene component DVSC is sent to each of the first and third output color channels. Those knowledgeable in the field understand that the operations described with respect to the augmented color correction process are done with respect to a subunit of a frame, e.g., on a pixel by pixel basis and that the "addition" is symbolic and may require undoing and redoing gamma correction for example to achieve a clear image.

Figure 6B:
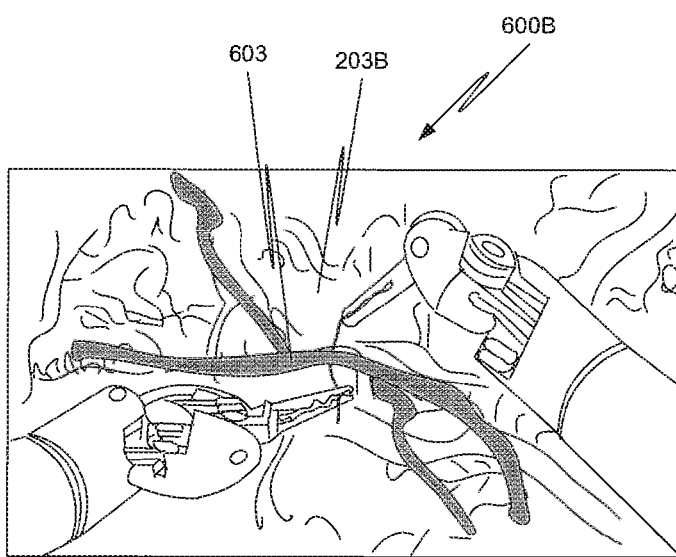
FIG. 6B is a representation of a reduced color stereoscopic image obtained using the system of FIG. 2 with a highlighted fluorescence image.

The outputs from augmented color correction module 232 are displayed on stereoscopic display 241 (FIG. 2) in GENERATE STEREOSCOPIC VIDEO DISPLAY OF TISSUE process 305 (FIG. 3). In the augmented viewing mode, processes 301 to 305 are performed repetitively on each acquired frame so that the surgeon sees a real-time video augmented image of surgical site 203. During the augmented viewing mode, the surgeon is provided with a three-dimensional reduced color scene 600B of surgical site 203B with region of interest 603 (FIG. 6B) highlighted in a particular color.

Figure 7:
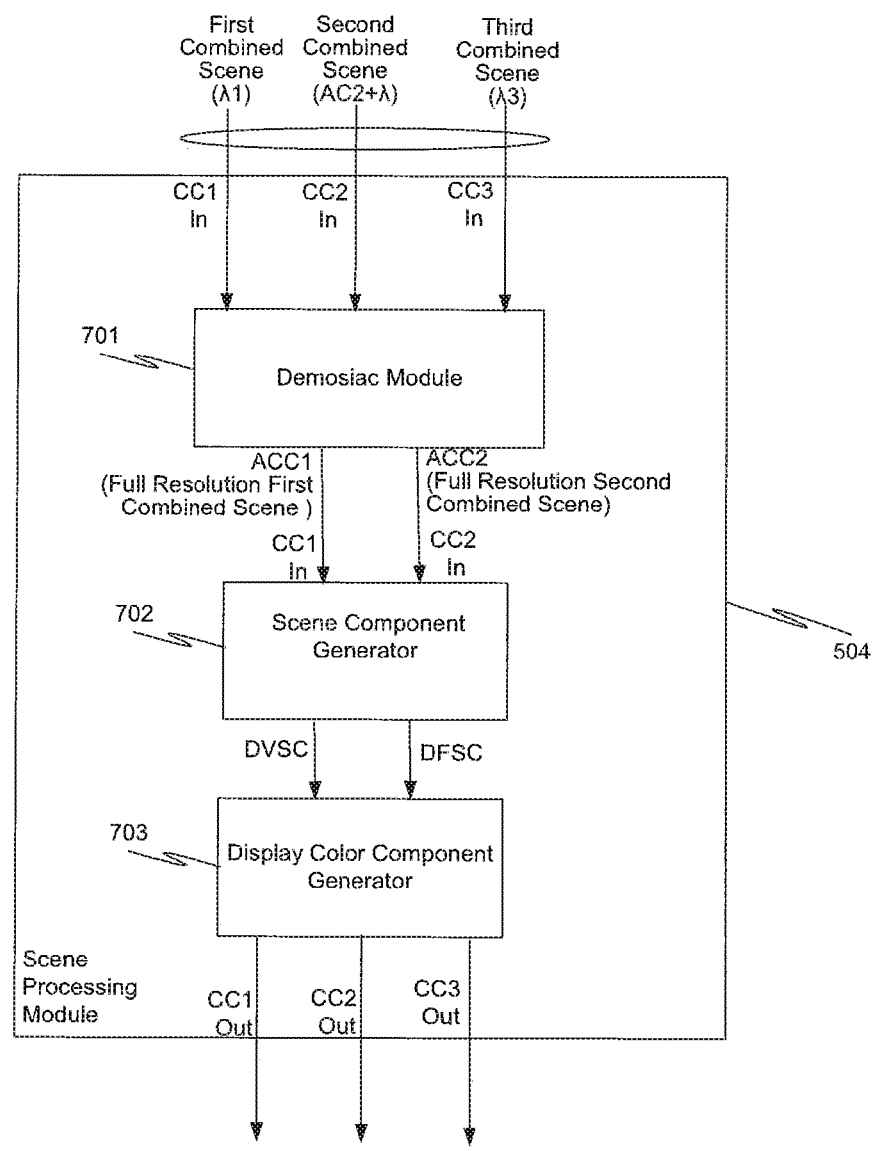
FIG. 7 is a more detailed block diagram of the scene processing module of FIG. 5.

FIG. 7 is a more detailed diagram of one aspect of scene processing module 504. Scene processing module 504 includes a demosaic module 701, a scene component generator 702, and a display color component generator 703.

Figure 8A:
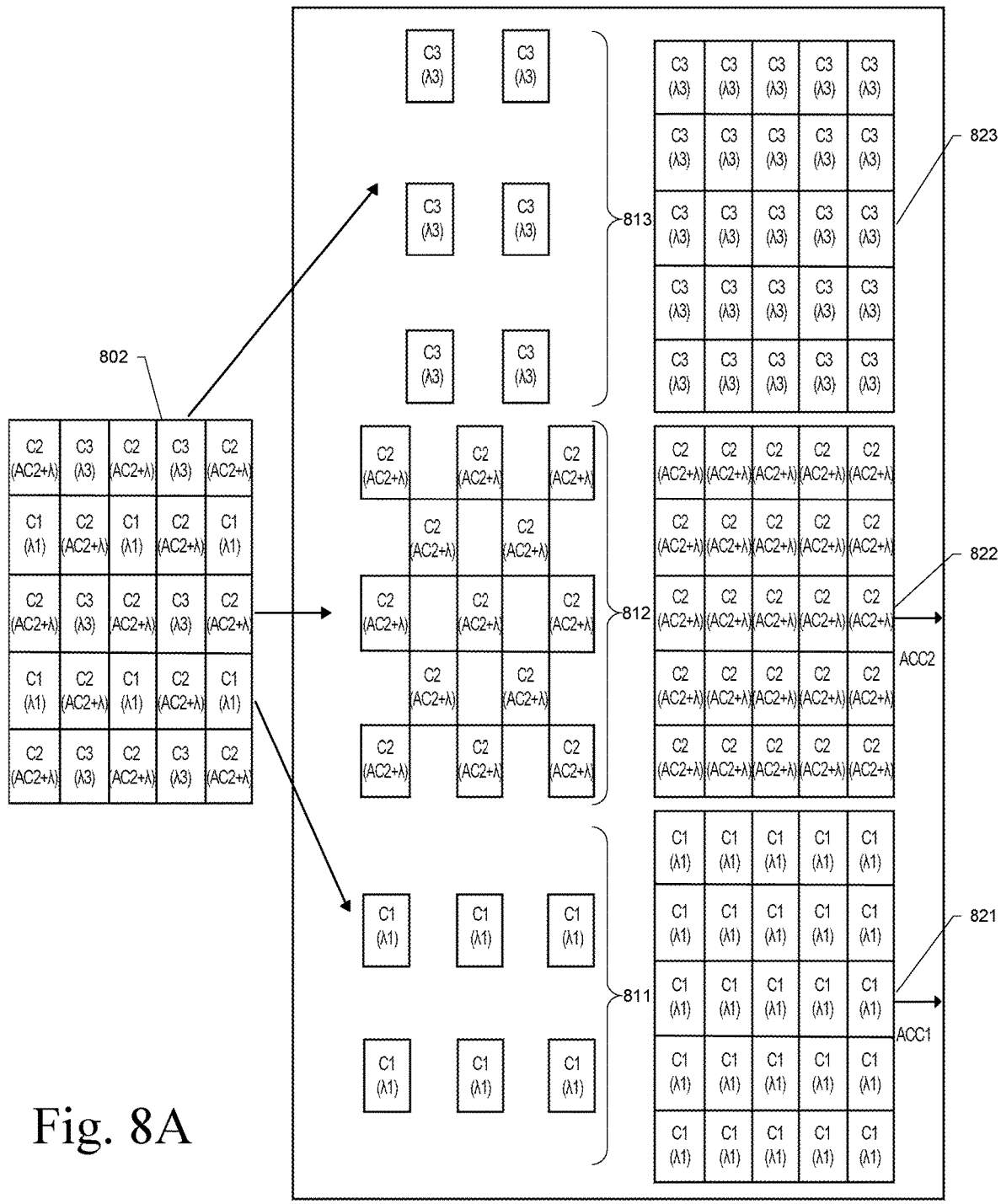
FIG. 8A illustrates input data to and the output data from the demosaic module of FIG. 7 in a first aspect.
Figure 8B:
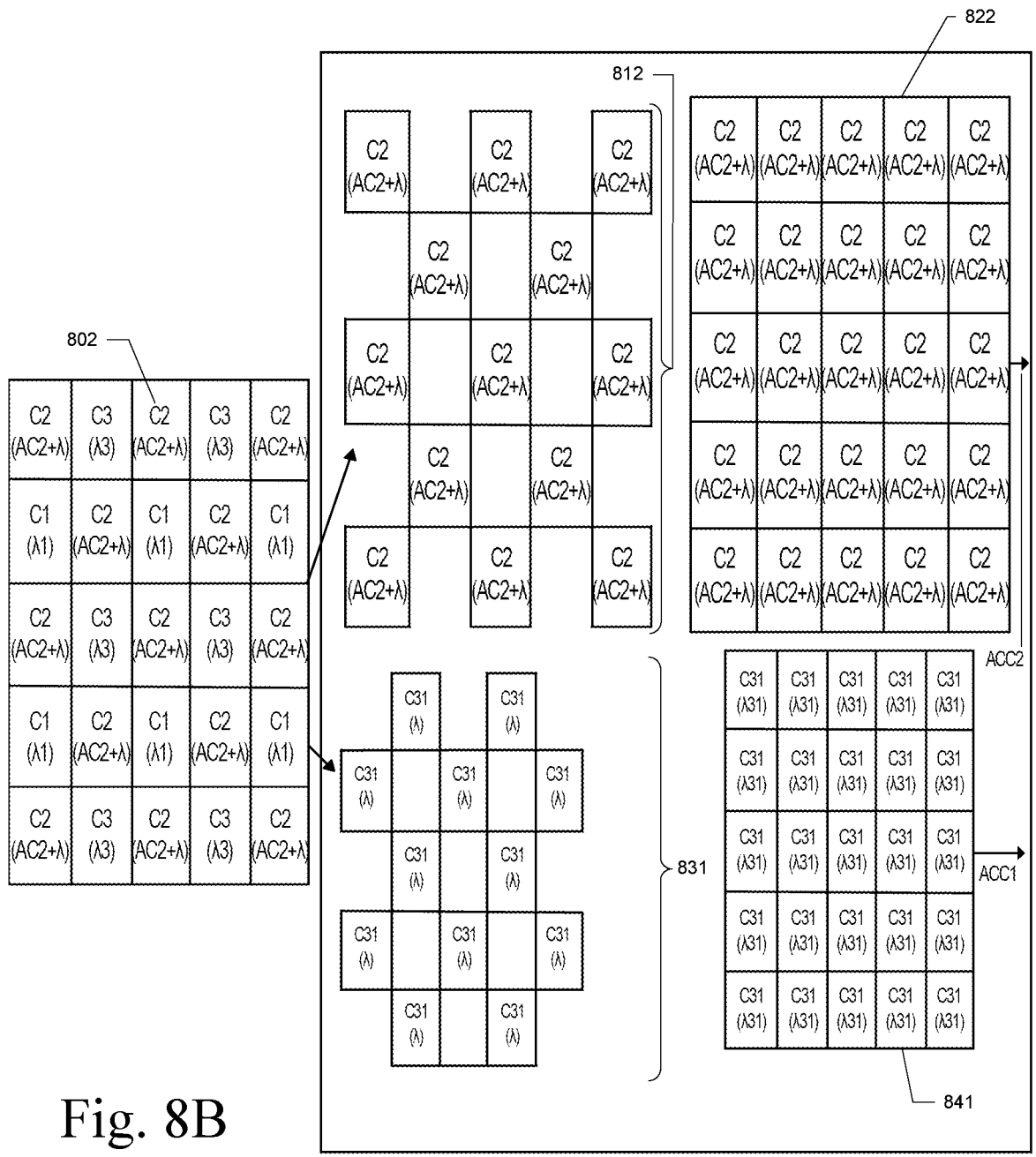
FIG. 8B illustrates input data to and the output data from the demosaic module of FIG. 7 in a second aspect.

FIGS. 8A and 8B are illustrations of input information to demosaic module 701 and output information from demosaic module 701. In FIG. 8A, acquired pixel data 802 is representative of a frame of pixel data captured by a single-chip image capture sensor having a Bayer color filter array. Again, in this example, three visible color components C1, C2, and C3 are used. Interpolation techniques used in demosaicing are known to those knowledgeable in the field and so are not considered in further detail.

A pixel in acquired pixel data 802 is represented by a square in FIGS. 8A and 8B. The color component in a square gives the color of the filter in the color filter array for that pixel, i.e., one of color C1, C2, and C3. The information enclosed within parentheses in a square is the light that is captured by the pixel in this example.

Since the fluorescence is in the near infrared spectrum, the fluorescence is passed through the filters in the color filter array for each of three visible color components C1, C2, and C3. Thus, each of the pixels captures the brightness of fluorescence scene component λ at the location of the pixel.

In this example, the visible color illumination component is color component C2. There is no illumination for visible color components C1 and C3. Light reflected from the tissue is color component C2 light and is passed through the filters in the color filter array that pass color component C2 light. The second visible color component C2 light is captured by the image capture sensor is acquired second visible color component scene AC2 in FIGS. 8A and 8B. Note that pixels for color components C1 and C3 can also capture some of the reflected color component C2 light if the reflected light leaks through the filters for color components C1 and C3 in the color filter array. This is why the scenes for color components C1 and C3 are referred to as combined scenes λ1 and λ3, respectively.

As illustrated in FIGS. 7, 8A, and 8B, in this aspect, demosaic module 701 receives a third set of pixel data 813 of color component C3 in the third color channel, and a first set of pixel data 811 of color component C1 in a first color channel. Third set of pixel data 813 includes third combined image λ3 that in turn includes fluorescence scene component λ. First set of pixel data 811 includes first combined image λ1 that in turn includes fluorescence scene component λ. Demosaic module 701 also receives, in the second color channel, the second combined image that includes a combination of acquired second visible color component scene AC2 and fluorescence scene component λ in a second set of pixel data 812 of color component C2.

Using the received pixel data in each color channel, in the aspect of FIG. 8A, demosaic module 701 generates a full resolution set of image pixel data for each of the three color components, which are represented by arrays 821 to 823. However, in one aspect, when only a single visible color component illumination source is used with a single fluorescence excitation illumination component, as in this example, only one of full resolution image pixel arrays for color components C1 and C3 is needed and so only the acquired pixel data for one of color components C1 and C3 is demosaiced. However, if a second visible color component illumination source is used or alternatively, a second fluorescence with a spectrum in the range of one of color component C1 and C3 is captured, the full demosaic process illustrated in FIG. 8A is used.

In another aspect, when only a single visible color component illumination is used with a single fluorescence excitation illumination component, demosaic module 701 combines the acquired pixel data of the two color components that includes fluorescence scene component λ and leakage data, and processes the combined pixel data as single color channel to generate a full resolution set of image pixel data comprising a fourth combined scene. In the example of FIG. 8A, the acquired data for pixels of color components C1 and C3 includes fluorescence scene component λ and leakage data. Thus, demosaic module 701 combines the pixel data in channels 811 and 813 in FIG. 8A and creates combined pixel data for a color channel 831. Demosaic module 701 processes the acquired data for color components C1 and C3 as a single color channel 831 and generate a full resolution set of image pixel data comprising a fourth combined scene λ31 (FIG. 8B). The pixel data in color channel 831 is illustrated in FIG. 8B as having color component C31.

Thus, in this aspect, two color channels 812, 831 are demosaiced to obtain a full resolution pixel array for each of the color channels. Since a larger number of acquired data locations are used in the demosaicing of the combined color channel, the accuracy of the full resolution data is improved relative to when only pixel data for a single color channel in the combined color channel is used in the demosaicing.

The transmission of the fluorescence through the different color component filters in the color filter array may not be the same. Thus, in one aspect, correction factors are used to scale the acquired pixel data for each color component so that the values that are demosaiced are equal for equal fluorescence. The correction factors are experimentally determined by capturing light from a known light source using the image capture sensor with the color filter array. The captured calibration pixel data is analyzed and scale factors determined so that the response is equal for each color component for equal fluorescence.

In this example, scene component generator 702 receives a first full resolution array ACC1 of image pixel data of combined scene λ1 that includes acquired fluorescence scene component λ, e.g., one of array 821 and array 841, in a first input color channel CC1. Scene component generator 702 also receives a second full resolution array ACC2 of image pixel data of the second combined scene that is a combination of acquired second visible color component scene AC2 and fluorescence scene component λ, i.e., array 822, in a second input color channel CC2.

Scene component generator 702 generates a display visual scene component DVSC and a display fluorescence scene component DFSC from the two full resolution arrays of image pixel data In one aspect, the extraction is represented as:

$$DFSC(x,y)=ACC1(x,y)-s2*ACC2(x,y) \qquad (1)$$

$$DVSC(x,y)=ACC2(x,y)-s1*ACC1(x,y) \qquad (2)$$

In general terms, display visual scene component DVSC is linear weighted combination of acquired second visible color component scene AC2 and fluorescence scene component λ. Display fluorescence scene component DFSC is a different linear weighted combination of acquired second visible color component scene AC2 and fluorescence scene component λ.

Definitions (1) and (2) indicate that the display visual scene component DVSC at location (x, y) is a weighted linear combination of the image pixel value in the first color channel and the image pixel value in the second color channel at location (x, y), where the image pixel value in the second color channel is a combination of the acquired fluorescence and visible scene components (AC2+λ) and the image pixel value in the first color channel is the first combined scene that includes acquired fluorescence scene component λ at location (x, y) combined with any leakage of second visible color component scene AC2 at location (x, y). Similarly, the display fluorescence scene component DFSC at location (x, y) is a weighted linear combination of the image pixel value in the first color channel and the image pixel value in the second color channel at location (x, y). Scale factors s1 and s2 used in the extraction can be determined in the same way as the scale factors described more completely below.

In this example, display color component generator 703 receives a full resolution display visual scene component DVSC and a full resolution display fluorescence scene component DFSC. Display color component generator 703 generates a final display color component for each of the color channel inputs to the display unit. Thus, a plurality of final display color components is generated. As explained above, each final display color component is a weighted linear combination of full resolution display visual scene component DVSC and a full resolution display fluorescence scene component DFSC.

Figure 9:
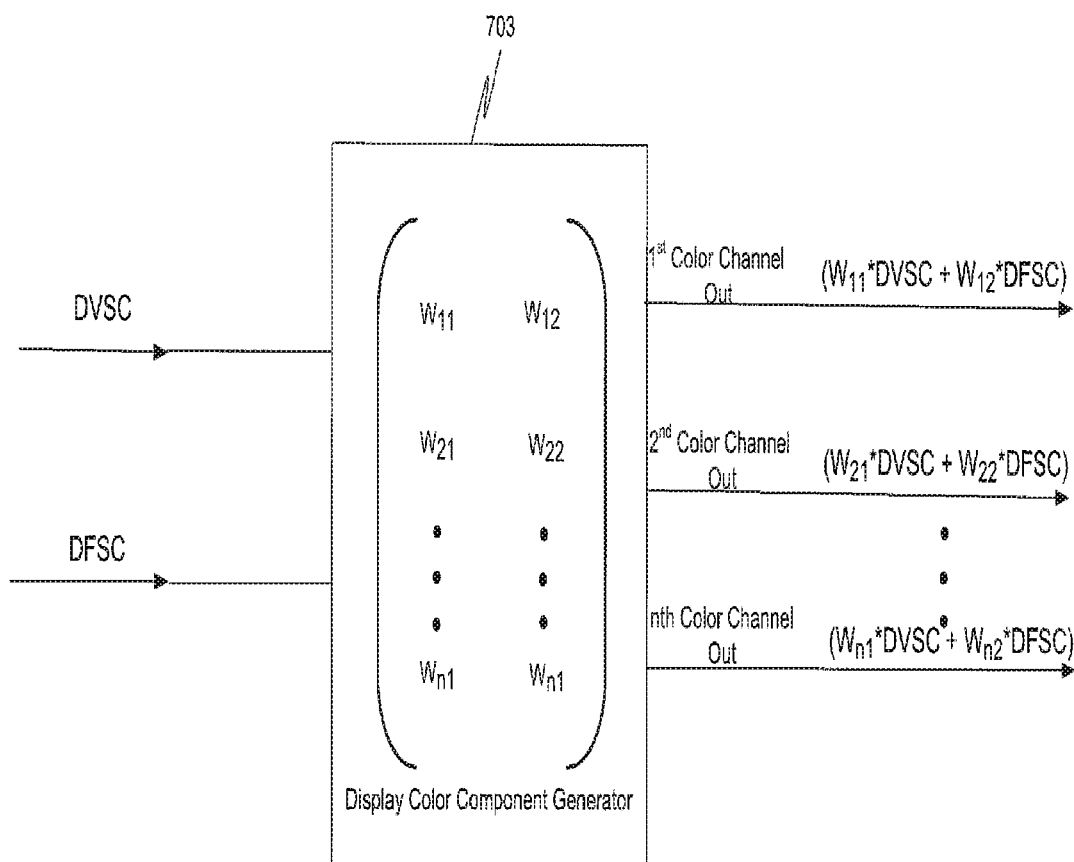
FIG. 9 is a more detailed block diagram of the display color component generator of FIG. 5.

In the example of FIG. 9, the display unit has n color component inputs, where n is a positive non-zero integer number. In the above example, n was taken as three. The weights $w_{ij}$ used in display color component generator 703 are selected to provide a display scene that includes a reduced color visible scene component combined with a fluorescence scene component with color characteristics that allow easy differentiation between the two scenes. Multiple factors can be taken into account in selecting the weights such as brightness, contrast, color separation, eye fatigue, etc.

Below, two examples are presented of obtaining scale factors for use in scene component generator 702. In the first example, the response of the image capture unit—the single-chip image capture sensor and color filter array—is determined for visible illumination VIS and for fluorescence excitation illumination NIR, separately. The response is defined as:

$$C_{VIS}(x,y) = \begin{bmatrix} CC_1(x,y) \\ CC_2(x,y) \\ \dots \\ CC_n(x,y) \end{bmatrix} = \begin{bmatrix} S_{11} & S_{12} & S_{13} & S_{1m} \\ S_{21} & S_{22} & S_{23} & S_{2m} \\ \dots & \dots & \dots & \dots \\ S_{n1} & S_{n2} & S_{n3} & S_{nm} \end{bmatrix} * \begin{bmatrix} E_{VIS1}(x,y) \\ E_{VIS2}(x,y) \\ \dots \\ E_{VISm}(x,y) \end{bmatrix} \quad (3)$$

$$C_{NIR}(x,y) = \begin{bmatrix} CC_1(x,y) \\ CC_2(x,y) \\ \dots \\ CC_n(x,y) \end{bmatrix} = \begin{bmatrix} S_{11} & S_{12} & S_{13} & S_{1m} \\ S_{21} & S_{22} & S_{23} & S_{2m} \\ \dots & \dots & \dots & \dots \\ S_{n1} & S_{n2} & S_{n3} & S_{nm} \end{bmatrix} * \begin{bmatrix} E_{NIR1}(x,y) \\ E_{NIR2}(x,y) \\ \dots \\ E_{NIRm}(x,y) \end{bmatrix} \quad (4)$$

where C(x, y) represents the n color component response of the single-chip image sensor,
S represents the image sensor responsivity functions,
E represents the spectral reflected light from the scene using visible illumination, or fluorescence from the scene excited by fluorescence excitation illumination,
m is the number of discrete wavelengths used to represent the wavelength distribution of the reflected light in a plot of reflected light intensity versus wavelength,
VIS represents visible illumination, and
NIR represents fluorescence excitation illumination.

Generating the image sensor responsivity functions is done using techniques know to those knowledgeable in the field and so is not considered in further detail.

A separation color matrix SCM is used in scene component generator 702 to extract display visible scene component DVSC and display fluorescence scene component DVSC from the received image pixel data. Separation color matrix SCM is defined as:

$$SCM(x,y) = pinv([C_{VIS}(x,y), C_{NIR}(x,y)]) \quad (5)$$

where pinv( ) is the pseudo inverse, and
[$C_{VIS}$(x, y), $C_{NIR}$(x, y)] is the concatenation of the two column vectors into an [n×2] matrix.

A matrix pseudo inverse is known to those knowledgeable in the field. A pseudo inverse suitable to use here is referred to as the Moore-Penrose pseudo inverse. A common use of the Moore-Penrose pseudo inverse is to compute a 'best fit' least squares solution to the system of linear equations, which lacks a unique solution. Another use of the Moore-Penrose pseudo inverse is to find the minimum (Euclidean) norm solution to the system of linear equations. In one aspect, the best fit least squares solution is used. However, other inverse methods exist that can lower the noise amplification of the separation color matrix.

Thus, in this aspect, the processing implemented in scene component generator 702 is:

$$\begin{bmatrix} DVSC(x,y) \\ DFSC(x,y) \end{bmatrix} = \begin{bmatrix} scm_{11} & scm_{12} & \dots & scm_{1k} \\ scm_{21} & scm_{22} & \dots & scm_{2k} \end{bmatrix} * \begin{bmatrix} ACC1(x,y) \\ ACC2(x,y) \\ \dots \\ ACCk(x,y) \end{bmatrix} \quad (6)$$

where ACCi(x, y) is a value of an image pixel at location (x, y) in the full resolution array for the ith color channel from demosaic module 701, where i ranges from 1 to k and k is the number of input color channels to scene component generator 702 that receive a full resolution array of image pixel data from the demosaic module 701,
scmij is a weight in the separation color matrix SCM,
DVSC(x, y) is a value of a pixel at location (x, y) in the display visual scene component DVSC, and
DFSC(x, y) is a value of a pixel at location (x, y) in the display fluorescence scene component DFSC.

In above example, the number of input color channel was taken as three and so $$\begin{bmatrix} DVSC(x,y) \\ DFSC(x,y) \end{bmatrix} = \begin{bmatrix} scm_{11} & scm_{12} & scm_{13} \\ scm_{21} & scm_{22} & scm_{23} \end{bmatrix} * \begin{bmatrix} ACC1(x,y) \\ ACC2(x,y) \\ ACCk(x,y) \end{bmatrix} \quad (7)$$

$$\begin{bmatrix} DVSC(x,y) \\ DFSC(x,y) \end{bmatrix} = \begin{bmatrix} scm_{11} & scm_{12} & scm_{13} \\ scm_{21} & scm_{22} & scm_{23} \end{bmatrix} * \begin{bmatrix} \{\lambda + fw1*AC2\}(x,y) \\ \{AC2 + \lambda\}(x,y) \\ \{\lambda + fw3*AC2\}(x,y) \end{bmatrix} \quad (8)$$

where (fw1*AC2) represents second color component light that leaks through the filter for the first color component in the color filter array, and (fw3*AC2) represents second color component light that leaks through the filter for the third color component in the color filter array.

Thus, at location (x, y), $$DVSC = scm_{11}*\{\lambda + fw1*AC2\} + scm_{12}*\{AC2+\lambda\} + scm_{13}*\{\lambda + fw3*AC2\} = (scm_{11}*fw1 + scm_{12} + scm_{13}*fw3)*AC2 - (-scm_{11} - scm_{12} - scm_{13})*\lambda \quad (9)$$

$$DFSC = scm_{21}*\{\lambda + fw1*AC2\} + scm_{22}*\{AC2+\lambda\} + scm_{23}*\{\lambda + fw3*AC2\} = (scm_{21} + scm_{22} + scm_{23})*\lambda - (-scm_{21}*fw1 - scm_{22} - scm_{23}*fw1)*AC2 \quad (10)$$

In above expression (7), the weights in separation color matrix SCM have been taken as positive values, but in practice some are negative. Also, the display components can be normalized so that these expressions are in the same form as those given above in expressions (1) and (2). Thus, the contribution of the acquired fluorescence scene component λ is removed from the displayed visual scene component DVSC and the contribution of the acquired second visible color component scene AC2 is removed from the displayed fluorescence scene component DFSC by scene component generator 702.

In another example, the following general imaging model is used.

$$\begin{bmatrix} ACC_1(x,y) \\ ACC_2(x,y) \\ \dots \\ ACC_n(x,y) \end{bmatrix} = \begin{bmatrix} a_{11} & a_{12} & a_{13} & \dots & a_{1(n+1)} \\ a_{21} & a_{22} & a_{23} & \dots & a_{2(n+1)} \\ \dots & \dots & \dots & \dots & \dots \\ a_{n1} & a_{n2} & a_{n3} & \dots & a_{n(n+1)} \end{bmatrix} * \begin{bmatrix} L_\lambda R_\lambda(x,y) \\ L_1 R_1(x,y) \\ L_2 R_2(x,y) \\ \dots \\ L_n Rn(x,y) \end{bmatrix} \quad (11)$$

where n is the number of color components in the color model of interest,
$L_i$, i=1 to n, represents visible color component illumination for the ith color component,
$R_i$, i=1 to n, represents reflectiveness of the surgical site at location (x, y) for the ith color component,
Lλ represents fluorescence excitation illumination,
Rλ represents fluorescence from the object in surgical scene at location (x, y)
$a_{ij}$ is weight in the general imaging model where j ranges from 1 to (n+1)
$ACC_i$(x, y) is a value of an image pixel at location (x, y) in the full resolution scene for the ith color component from demosaic module 701, where i ranges from 1 to n.

A constraint imposed on the image model defined in expression (11) is that the weights $a_{ij}$ are global and constant at all pixel locations (x, y). The values of weights $a_{ij}$ are a function of the image capture unit, but as explained below their actual values are not needed to determine scale factors s1 and s2 in expressions (1) and (2) above, because scale factors s1 and s2 are determined by a calibration process, as described more completely below.

In the above examples, fluorescence excitation illumination and a second visible color illumination component were used and the illumination for the other visible color components is zero, e.g., $$L_1=L_3=\ldots=L_n=0 \qquad (12)$$

Note that if one or more of the visible color illumination components are not exactly zero, the method described with the separation color matrix can be used.

When the other visible color illumination components are zero, the above system of equations (11) reduces to:

$$ACC_1(x, y) = a_{11}L_\lambda R_\lambda(x, y) + a_{13}L_2R_2(x, y) \qquad (13)$$

$$ACC_2(x, y) = a_{21}L_\lambda R_\lambda(x, y) + a_{23}L_2R_2(x, y)$$

$$\ldots$$

$$ACC_n(x, y) = a_{n1}L_\lambda R_\lambda(x, y) + a_{n3}L_2R_2(x, y)$$

However, when n is three and the first and third color channels are demosaiced as a single color channel, only the full resolution image pixel data arrays for $ACC_1(x, y)$ and $ACC_2(x, y)$ are generated by demosaic module 701. Recall that in the above examples, the image pixel data in full resolution array $ACC_1$ is the combination of fluorescence scene component λ and color filter leakage of second visible color component scene $AC_2$, and the image pixel data in the second full resolution array $ACC_2$ is the combination of second visible color component scene AC2 and fluorescence scene component λ.

Using definition (2) above, which is $$DVSC(x,y)=ACC_2(x,y)-s_1ACC_1(x,y)$$

and substituting for $ACC_1(x, y)$ and $ACC_2(x, y)$ from equation set (13) gives $$DVSC(x, y) =$$
$$(a_{21}L_\lambda R_\lambda(x, y) + a_{23}L_2R_2(x, y)) - s_{1*}(a_{11}L_\lambda R_\lambda(x, y) + a_{13}L_2R_2(x, y)) =$$
$$(a_{21} - s_1 a_{11})L_\lambda R_\lambda(x, y) + (a_{23} - s_1 a_{13})L_2R_2(x, y)$$

when $(a_{21}-s_1 a_{11})$ equals zero, this reduces to $$DVSC(x,y)=(a_{23}-s_1 a_{13})L_2R_2(x,y)$$

and the fluorescence scene component is removed from displayed visual scene component DVSC.

Also, using definition (1) above, which is $$DFSC(x,y)=ACC_1(x,y)-s_2ACC_2(x,y)$$

and substituting for $ACC_1(x, y)$ and $ACC_2(x, y)$ from equation set (13) gives $$DFSC(x, y) = (a_{11}L_\lambda R_\lambda(x, y) + a_{13}L_2R_2(x, y)) -$$
$$s_{2*}(a_{21}L_\lambda R_\lambda(x, y) + a_{23}L_2R_2(x, y))$$
$$= (a_{11} - s_2 a_{21})L_\lambda R_\lambda(x, y) +$$
$$(a_{13} - s_2 a_{23})L_2R_2(x, y)$$

when $(a_{13}-s_2 a_{23})$ equals zero, this reduces to $$DFSC(x,y)=(a_{11}-s_2 a_{21})L_\lambda R_\lambda(x,y)$$

and the visible scene component is removed from displayed fluorescence scene component DFSC.

Thus, scale factor $s_2$ is defined as, $$s_2=a_{13}/a_{23} \text{ and}$$

scale factor $s_1$ is defined as $$s_1=a_{21}/a_{11}$$

To estimate scale factor $s_1$ and scale factor $s_2$, a calibration process is used. A second visible color component illumination source and a fluorescence excitation illumination source are used, in one aspect.

Specifically, when fluorescence excitation illumination source $L_\lambda$ is non-zero and all other illumination sources are zero, equation set (13) reduces to:

$$ACC_1(x, y) = a_{11}L_\lambda R_\lambda(x, y)$$

$$ACC_2(x, y) = a_{21}L_\lambda R_\lambda(x, y)$$

$$\ldots$$

$$ACCn(x, y) = a_{n1}L_\lambda R_\lambda(x, y)$$

Dividing the second equation by the first equation gives:

$$s_1(x,y)=a_{21}/a_{11}=ACC_2(x,y)/ACC_1(x,y)$$

Thus, scale factor $s_1(x, y)$ is the ratio of the pixel value for the second color component to the pixel value for the first color component at a location captured by the image capture sensor when only fluorescence excitation illumination is used.

To provide a simple robust estimation of scale factor $s_1$, pixel data having a value of zero are not used in determining scale factor $s_1$. Also, to obtain single constant scale factor $s_1$ in definition (1), averaging over $s_1(x, y)$ is performed. In averaging over $s_1(x, y)$ to obtain the single constant scale factor $s_1$, outliers, such as zero pixels and saturation pixels, are removed because the linearity is broken for such pixels. In one aspect, a value of 0.9 was used for scale factor $s_1$. Thus, the scale factor is estimated based on a ratio of images captured for a specific illumination source.

Similarly, when illumination source $L_2$ is non-zero and all other illumination sources are zero, equation set (13) reduces to:

$$ACC_1(x, y) = a_{13}L_2R_2(x, y)$$

$$ACC_2(x, y) = a_{23}L_2R_2(x, y)$$

$$\ldots$$

$$ACCn(x, y) = a_{n3}L_2R_2(x, y)$$

Dividing the first equation by the second equation gives:

$$s_2(x,y)=a_{13}/a_{23}=ACC_1(x,y)/ACC_2(x,y)$$

Thus, scale factor $s_2(x, y)$ is the ratio of the pixel value for the first color component to the pixel value for the second color component at a location captured by the image capture sensor when only second color component illumination is used. Again, to obtain single constant scale factor $s_2$, in definition (1) averaging over $s_2(x, y)$ is performed. In averaging over $s_2(x, y)$ to obtain single constant scale factor $s_2$, outliers, such as zero pixels and saturation pixels, are removed because the linearity is broken for such pixels. In one aspect, a value of 0.2 was used for scale factor $s_2$. Thus, the scale factor is estimated based on a ratio of images captured for a specific illumination source.

With the values of scale factors scale factor $s_1$ and scale factor $s_2$, expressions (1) and (2) above are used to extract display visual scene component DVSC and a display fluorescence scene component DFSC. In this example, if the image capture sensor is saturated or close to saturation, expressions (1) and (2) do not give the correct result. This is because the linearity assumption in the imaging model of expression (11) is broken. Thus, illumination levels and image capture unit gain control are configured to minimize saturation. For pixels that are nevertheless saturated, the saturated pixels are detected and expressions (1) and (2) are not used at these locations. Instead, a pure white pixel value with no fluorescence is assigned to these locations to indicate the saturation status.

In the above examples, a single visible color illumination component and a single fluorescence excitation illumination component were used. As stated previously, the processes described above work with a single-chip image capture sensor with a color filter array and other combinations of illumination. For example, for n visible color components that make up white light, some of the possible combination are:

(n–1) or less visible color illumination components and a fluorescence illumination excitation component, where the fluorescence is either outside the visible spectrum, or in the wavelength range of the nth color component, where the nth color component is the one for which no visible illumination was provided; and (n–2) or less visible color illumination components and two different fluorescence illumination excitation components that excite fluorescence either in the wavelength range of the nth and (n–1) visible color components, where the nth and (n–1) color components are the ones which contain no visible illumination, or that excite in the wavelength range of the nth visible color component and outside the visible spectrum, where the nth color component is the one that contains no visible illumination.

The processing of the data for these combinations is similar to that described above, except extra components must be considered that correspond to the additional pixel data that is captured. Also, the leakage characteristics of the color filter array are considered to determine the extra components that must be captured.

For example if there are red, green, and blue color components and the fluorescence is in the blue spectrum, the blue pixel data represents the fluorescence scene component. The green pixel data represents a combination of a green scene component and the fluorescence scene component. The red pixel data represents a red scene component. The acquired data is processed as described above, except for this example, the red pixel data does not include fluorescence and so the leakage weight for the fluorescence in the combined scene for the red color component is zero.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text. For example, a surgical system is used as an example. However, the mixed mode imaging implemented using a single-chip image capture sensor with a color filter array as described herein can be implemented in any system that includes the components, assemblies, etc. used in the mixed mode imaging.

The various modules described herein can be implemented by software executing on a processor, hardware, firmware, or any combination of the three. When the modules are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various modules, as described herein, may be performed by one unit, or divided up among different components, each of which may be implemented in turn by any combination of hardware, software that is executed on a processor, and firmware. When divided up among different components, the components may be centralized in one location or distributed across system 200 for distributed processing purposes. The execution of the various modules results in methods that perform the processes described above for the various modules and controller 130.

Thus, a processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a non-transitory tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives and other physical storage mediums.

In view of this disclosure, instructions used in any part of or all of the processes described herein can be implemented in a wide variety of computer system configurations using an operating system and computer programming language of interest to the user.

Herein, first and second are used as adjectives to distinguish between elements and are not intended to indicate a number of elements. Also, top, bottom, and side are used as adjectives to aid in distinguishing between elements as viewed in the drawings, and to help visualize relative relationships between the elements. For example, top and bottom surfaces are first and second surfaces that are opposite and removed from each other. A side surface is a third surface that extends between the first and second surfaces. Top, bottom, and side are not being used to define absolute physical positions.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

What is claimed is:

1. A method comprising:
   receiving a single frame comprising:
      a first set of pixel data that includes a fluorescence scene component, and
      a second set of pixel data that includes a combination of a visible color component scene and the fluorescence scene component; and
   generating, based on the first set of pixel data that includes the fluorescence scene component and the second set of pixel data that includes the combination of the visible color component scene and the fluorescence scene component, a display scene.

2. The method of claim 1, further comprising:
   providing first and second illumination components to illuminate, at a same time, a scene represented by the single frame, wherein:
      the first illumination component includes a fluorescence excitation illumination component, and
      the second illumination component includes visible light that includes less than all visible color components of white light.

3. The method of claim 1, further comprising capturing the single frame using a single-chip image capture sensor having a color filter array.

4. The method of claim 3, wherein the capturing the single frame comprises:
   capturing the first set of pixel data with a first set of pixels of the single-chip image capture sensor, the first set of pixels associated with a first color filter included in the color filter array; and
   capturing the second set of pixel data with a second set of pixels of the single-chip image capture sensor, the second set of pixels associated with a second color filter included in the color filter array.

5. The method of claim 4, wherein:
   the first color filter is configured to allow light having a first color and fluorescence that results from fluorescence excitation illumination to pass through the first color filter to the first set of pixels; and
   the second color filter is configured to allow light having a second color and the fluorescence to pass through the second color filter to the second set of pixels.

6. The method of claim 4, wherein the second set of pixels are covered by a green color filter included in the color filter array.

7. The method of claim 4, wherein the second set of pixels are covered by a blue color filter included in the color filter array.

8. The method of claim 1, further comprising:
   receiving, in a first color channel, the first set of pixel data; and
   demosaicing the first set of pixel data to obtain a first set of image pixel data.

9. The method of claim 8, further comprising:
   receiving, in a second color channel, the second set of pixel data; and
   demosaicing the second set of pixel data to obtain a second set of image pixel data.

10. The method of claim 9, further comprising:
    determining, based on the first and second sets of image pixel data, a display fluorescence scene component and a display visible scene component;
    wherein the generating the display scene is based on the display fluorescence scene component and the display visible scene component.

11. The method of claim 10, wherein the display fluorescence scene component comprises a first linear weighted combination of the first set of image pixel data and the second set of image pixel data.

12. The method of claim 11, wherein the display visible scene component comprises a second linear weighted combination of the first set of image pixel data and the second set of image pixel data.

13. The method of claim 1, wherein the display scene includes:
    a highlighted scene component corresponding to the fluorescence scene component; and
    a reduced color scene component.

14. A system comprising:
    a memory storing instructions; and
    one or more processors communicatively coupled to the memory and configured to execute the instructions to perform a process comprising:
       receiving a single frame comprising:
          a first set of pixel data that includes a fluorescence scene component, and a second set of pixel data that includes a combination of a visible color component scene and the fluorescence scene component; and generating, based on the first set of pixel data that includes the fluorescence scene component and the second set of pixel data that includes the combination of the visible color component scene and the fluorescence scene component, a display scene.

15. The system of claim 14, wherein the process further comprises:

providing first and second illumination components to illuminate, at a same time, a scene represented by the single frame, wherein:

the first illumination component includes a fluorescence excitation illumination component, and the second illumination component includes visible light that includes less than all visible color components of white light.

16. The system of claim 14, wherein the single frame is captured using a single-chip image capture sensor having a color filter array.

17. The system of claim 14, wherein the process further comprises:

receiving, in a first color channel, the first set of pixel data; and demosaicing the first set of pixel data to obtain a first set of image pixel data.

18. The system of claim 17, wherein the process further comprises:

receiving, in a second color channel, the second set of pixel data; and demosaicing the second set of pixel data to obtain a second set of image pixel data.

19. The system of claim 18, wherein the process further comprises:

determining, based on the first and second sets of image pixel data, a display fluorescence scene component and a display visible scene component;

wherein the generating the display scene is based on the display fluorescence scene component and the display visible scene component.

20. A non-transitory computer-readable medium storing instructions that, when executed, direct a processor of a computing device to perform a process comprising:

receiving a single frame comprising:

a first set of pixel data that includes a fluorescence scene component, and a second set of pixel data that includes a combination of a visible color component scene and the fluorescence scene component; and generating, based on the first set of pixel data that includes the fluorescence scene component and the second set of pixel data that includes the combination of the visible color component scene and the fluorescence scene component, a display scene.

* * * * *